(12) United States Patent
Botton et al.

(10) Patent No.: US 9,102,632 B2
(45) Date of Patent: Aug. 11, 2015

(54) PYRAZINONE DERIVATIVES AS INSULIN SECRETION STIMULATORS, METHODS FOR OBTAINING THEM AND USE THEREOF FOR THE TREATMENT OF DIABETES

(71) Applicant: Merck Patent GmbH, Darmstadt (DE)

(72) Inventors: Gerard Botton, Buc (FR); Micheline Kergoat, Bures-sur-Yvette (FR); Christine Charon, Gometz-le-Chatel (FR); Samer Elbawab, Bures-sur-Yvette (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/109,225

(22) Filed: Dec. 17, 2013

(65) Prior Publication Data

US 2014/0100235 A1 Apr. 10, 2014

Related U.S. Application Data

(62) Division of application No. 12/920,932, filed as application No. PCT/EP2009/000213 on Jan. 15, 2009, now Pat. No. 8,637,522.

(30) Foreign Application Priority Data

Mar. 5, 2008 (EP) .................................. 08004193

(51) Int. Cl.
*C07D 241/08* (2006.01)
*C07D 241/18* (2006.01)

(52) U.S. Cl.
CPC ............ *C07D 241/08* (2013.01); *C07D 241/18* (2013.01)

(58) Field of Classification Search
CPC .................................................... C07D 241/08
See application file for complete search history.

(56) References Cited

U.S. PATENT DOCUMENTS

| 4,296,114 A | 10/1981 | Appleton et al. |
| 6,159,980 A | 12/2000 | Arvanitis et al. |

FOREIGN PATENT DOCUMENTS

| GB | 1471804 A | 4/1977 |
| WO | 2007071646 A1 | 6/2007 |
| WO | 2009009501 A2 | 1/2009 |

OTHER PUBLICATIONS

Bhattacharya, B.K. "Synthesis of some new 5-chloro-7-mercapto-1-methyl/phenyl-1, 2, 4-triazolo [4,5-b]pyrazin-2(1H)-ones and 5-chloro-3-thiopyrazin-2(1H)-one derivatives as possible antibacterial and antifungal agents." (Journal of Heterocyclic Chemistry), 1986, 113-118, 23:1.

Sharma et al. "A convenient microwave-assisted desulfitative dimethylamination of the 2(1H) pyrazinone scaffold using N,N-dimethyl formamide." (Tetrahedron), Jan. 11, 2008, 2605-2610, 64:11.

Singh, Brajendra Kumar et al. "Copper (II)-Mediated Cross-Coupling of Arylboronic Acids and 2(1H)-Pyrazinones Facilitated by Microwave Irradiation with Simultaneous Cooling." (Organic Letters), 2006, 1863-1866, 8:9.

World Intellectual Property Organization. "International Search Report." PCT/EP2009/000213, Applicant: Merck Patent GmbH., Mailed May 12, 2009.

Chung et al. "Synthesis of 3-Aminopyrazinone Mediated by 2-Pyridylthioimidate-ZnCl2 Complexes", Development of an Efficient Route to a Thrombin Inhibitor, 2003, Journal of Organic Chemistry, 68, 8838.

Parlow et al. Design, Parallel Synthesis, and Crystal Structures of Pyrazinone Antithrombotics as Selective Inhibitors of the Tissue Factor Vlla Complex, Journal of Medicinal Chemistry (2003), 46(19), 4050-4062.

Varma, R.K. et al., "Reaction of 3-Hydrazino Quinoxalin-2-(1H)-One With Aromatic/Carboxylic Acids Using Diphenyl Phosphoryl Azide: Synthesis & Antiallergic Activity of s-Triazolo[4,3-a] Quinoxalin-4-Ones", Indian Journal of Heterocyclic Chemistry vol. 3, Apr.-Jun. 1994, pp. 227-232.

*Primary Examiner* — Brian McDowell
(74) *Attorney, Agent, or Firm* — Millen, White, Zelano & Branigan, P.C.

(57) ABSTRACT

The treatment of diabetes and associated pathologies is achieved by administering the pyrazinone compounds of formula (I)

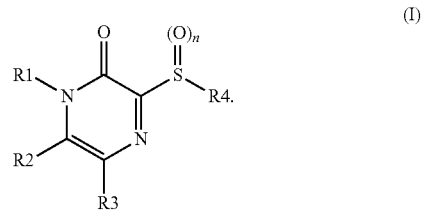

24 Claims, No Drawings

PYRAZINONE DERIVATIVES AS INSULIN SECRETION STIMULATORS, METHODS FOR OBTAINING THEM AND USE THEREOF FOR THE TREATMENT OF DIABETES

FIELD OF THE INVENTION

The present invention relates to pyrazinone derivatives of formula (I) as insulin secretion stimulators. The invention also relates to the preparation and use of these pyrazinone derivatives for the prophylaxis and/or treatment of diabetes and pathologies associated.

BACKGROUND OF THE INVENTION

Type 2 diabetes mellitus is one of the most common worldwide diseases. In 2007, its prevalence was estimated at 5.9% (246 million people) of the adult population and is in continuous increase. This disease is even more serious since it could lead to severe micro- and macro-complications, which could become disabling or lethal, as diabetes is a major risk factor for cardiovascular disease and stroke.

Type 2 diabetes is characterized by a fasted and postprandial hyperglycemia, consequence of two main defects: an insulin resistance at the level of target tissues and an altered insulin secretion from the pancreatic beta cells. This latter anomaly seems to appear very as it is present at the Impaired Glucose Tolerance (IGT) stage (Mitrakou et al., N. Engl. J. Med. 326: 22-29, 1992). It has been observed in UK Prospective Diabetes Study (UKPDS) that 50% of the beta cell function is already lost when diabetes is diagnosed, suggesting that deterioration in beta cell function may begin 10-12 years before diabetes diagnosis (Holman, *Diabetes Res. Clin. Pract.* 40: S21, 1998 or *UKPDS Group, Diabetes* 44: 1249-58, 1995).

The defective insulin secretion is due to a quantitative and a qualitative defect of the beta cell, i.e. a decreased beta cell mass and a specific defect of insulin release in response to glucose, especially the first phase of secretion, since the response to non-glucose secretagogues is preserved (Pfeifer et al., Am. J. Med. 70: 579-88, 1981). The importance of restoring a normal profile of insulin release in response to glucose to maintain the glycemic control within a normal range was supported by studies in non diabetic volunteers showing that delaying the first phase of insulin secretion in response to glucose led to glucose intolerance (Calles-Escandon et al., Diabetes 36: 1167-72, 1987).

Oral antidiabetics available for treatment of type 2 diabetic patients, such as sulfonylureas or glinides, are known to induce insulin secretion, by binding to sulfonylurea receptor on the K-ATP channels of the beta cell, leading to increase in intracellular calcium and insulin exocytosis. This insulin release is thus totally independent of the plasma glucose level and treatment with these molecules usually induces sustained hyperinsulinemia, which could lead to several side-effects, such as severe hypoglycaemia, body weight gain, and aggravation of cardiovascular risk. In addition, the prolonged hyperinsulinemia observed with sulfonylurea treatment, with no preservative effect of the beta cell mass, could lead to secondary failure due to beta cell exhaustion, another deleterious side effect of these compounds.

New treatment of type 2 diabetes should restore a normal profile of insulin release specifically in response to glucose, while preserving or increasing the beta cell mass. This is observed with GLP-1 analogs, such as exenatide or liraglutide, but these molecules are peptides and must be administered by parenteral route.

Such characteristics for a new oral small molecule would be a great advantage over the other antidiabetic drugs.

According to the present invention, the compounds of the formula (I) are insulin secretion stimulators, useful for treatment of diabetes and pathologies associated. They lower blood glucose levels by restoring the defective glucose-induced insulin secretion in type 2 diabetics.

The patent application WO 2007071646 describes aryl and heteroaryl substituted pyrazinone derivatives having antagonistic melanin-concentrating hormone activity, usefull for the prevention and/or treatment of psychiatric disorders.

EP 927171 describes pyrazinones corticotrophin releasing factor antagonists for use in treating psychiatric and neurological diseases including major depression, anxiety-related disorders, post-traumatic stress disorders and eating disorders.

SUMMARY OF THE INVENTION

The present invention is directed towards pyrazinone derivatives of formula (I). Said derivatives are useful for treating diabetes and pathologies associated therewith. Pyrazinone derivatives according to the invention have the following formula (I):

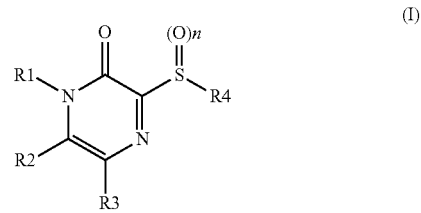

wherein:

n=0, 1, 2;

R1 is selected from hydrogen, heteroaryl, Z;

R2 is selected from hydrogen, halogen, heteroaryl, Z;

R3 is selected from hydrogen, halogen, aryl, heteroaryl, Z;

wherein aryl and heteroaryl groups can be optionally substituted by one or more substituents selected from Y;

R2 and R3 can constitute a cycle, saturated or not, optionally substituted by any substituent selected from Z;

R4 is selected from:

Z;

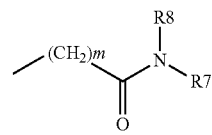

wherein:

m=1-6;

R7 and R8 are independently selected from:

hydrogen, aryl, heteroaryl, Z;

wherein aryl and heteroaryl groups can be optionally substituted by one or more substituents selected from Y;

R7 and R8 together can constitute an heterocycle; the heterocycle can include one or more heteroatom from N, O and S;

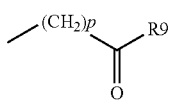

wherein:
p=1-6;
R9 is selected from:
aryl, heteroaryl, O—R10, Z;
wherein aryl and heteroaryl groups can be optionally substituted by one or more substituents selected from Y;
R10 is selected from:
hydrogen, alkyl, aryl, arylalkyl;
wherein alkyl, aryl, arylalkyl groups can be optionally substituted by one or more substituents selected from Y;
Z is selected from:
alkyl, alkenyl, alkynyl, aryl, arylalkyl, aryloxyalkyl, arylalkoxyalkyl, arylthioalkyl, arylalkylthioalkyl, heteroaryl, heteroarylalkyl, heteroaryloxyalkyl, heteroarylalkoxyalkyl, heteroarylthioalkyl, heteroarylalkylthioalkyl, heterocycloalkyl, heterocycloalkylalkyl, heterocycloalkyloxyalkyl, heterocycloalkylalkoxyalkyl, heterocycloalkylthioalkyl, heterocycloalkylalkylthioalkyl, arylalkenyl, arylalkynyl, cycloalkyl, cycloalkylalkyl, cycloalkyloxyalkyl, cycloalkylalkoxyalkyl, cycloalkylthioalkyl, cycloalkylalkylthioalkyl;
each of these groups can be optionally substituted by one or more substituents selected from Y;
heteroaryl and heterocycloalkyl groups can include one or more heteroatom from N, O and S;
Y is selected from:
hydroxy, thio, halogen, cyano, trifluoromethoxy, trifluoromethyl, carboxy, carboxy methyle, carboxyethyle, alkyle, alkoxy, alkylamino, aryl, aryl sulfonylalkyl, aryloxy, arylalkoxy, amino, NR5R6, azido, nitro, guanidino, amidino, phosphono, oxo, carbamoyle, alkylsulfonyl, alkylsulfinyl, alkylthio, two Y groups can form a mehylenedioxy;
wherein R5 and R6 are independently selected from:
hydrogen, alkyl, aryl, arylalkyl, heteroaryl, heteroarylalkyl;
wherein alkyl, aryl and heteroaryl groups can be optionally substituted by one or more substituents selected from Y;
R5 and R6 together can constitute an heterocycle; the heterocycle can include one or more heteroatom from N, O and S;
other preferred compounds are compounds of general formula (I) wherein R4 is not an aryl or an heteroaryl group;
as well as its racemic forms, tautomers, enantiomers, diastereomers, epimers and polymorphs, and mixtures thereof, and the pharmaceutically acceptable salts thereof.

In another preferred embodiment, the invention provides pyrazinone derivatives of formula (I), wherein:
n=0, 1, 2;
R1 is selected from:
hydrogen, alkyl, arylalkyl, aryloxyalkyl, arylalkoxyalkyl, heteroaryl, heteroarylalkyl, heteroaryloxyalkyl, heteroarylalkoxyalkyl, cycloalkyl, cycloalkylalkyl, cycloalkyloxyalkyl, cycloalkylalkoxyalkyl, heterocycloalkyl, heterocycloalkylalkyl, heterocycloalkyloxyalkyl, heterocycloalkylalkoxyalkyl; each of these groups can be optionally substituted by one or more substituents selected from Y;
heteroaryl and heterocycloalkyl groups can include one or more heteroatom from N, O and S;
R2 is selected from:
hydrogen, halogen, alkyl;
wherein alkyl groups can be optionally substituted by one or more substituents selected from Y;
R3 is selected from:
hydrogen, halogen, alkyl, aryl, heteroaryl, cycloalkyl, heterocycloalkyl;
wherein alkyl, aryl, heteroaryl, cycloakyl, heterocycloalkyl groups can be optionally substituted by one or more substituents selected from Y;
R2 and R3 can constitute a cycle, saturated or not, optionally substituted by any substituent selected from Y;
R4 is selected from:
Z, wherein Z is:
alkyl, arylalkyl, aryloxyalkyl, arylalkoxyalkyl, heteroarylalkyl, heteroaryloxyalkyl, heteroarylalkoxyalkyl, cycloalkyl, cycloalkylalkyl, cycloalkyloxyalkyl, cycloalkylalkoxyalkyl, heterocycloalkyl, heterocycloalkylalkyl, heterocycloalkyloxyalkyl, heterocycloalkylalkoxyalkyl;
each of these groups can be optionally substituted by one or more substituents selected from Y;
heteroaryl and heterocycloalkyl groups can include one or more heteroatom from N, O and S;

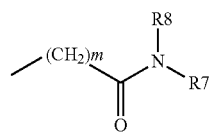

wherein:
m=1-6;
R7 and R8 are independently selected from:
hydrogen, aryl, heteroaryl, Z;
wherein aryl and heteroaryl groups can be optionally substituted by one or more substituents selected from Y;
R7 and R8 together can constitute an heterocycle; the heterocycle can include one or more heteroatom from N, O and S;

wherein:
p=1-6;
R9 is selected from:
aryl, heteroaryl, O—R10, Z;
wherein aryl and heteroaryl groups can be optionally substituted by one or more substituents selected from Y;
R10 is selected from:
hydrogen, alkyl, aryl, arylalkyl;
wherein alkyl, aryl, arylalkyl groups can be optionally substituted by one or more substituents selected from Y;
Y is selected from:
hydroxy, thio, halogen, cyano, trifluoromethoxy, trifluoromethyl, carboxy, carboxy methyle, carboxyethyle, alkyle, alkoxy, alkylamino, aryl, aryl sulfonylalkyl, aryloxy, arylalkoxy, amino, NR5R6, azido, nitro, guanidino, amidino, phosphono, oxo, carbamoyle, alkylsulfonyl, alkylsulfinyl, alkylthio, two Y groups can form a methylenedioxy;
wherein R5 and R6 are independently selected from:
hydrogen, alkyl, aryl, arylalkyl, heteroaryl, heteroarylalkyl;
wherein alkyl, aryl and heteroaryl groups can be optionally substituted by one or more substituents selected from Y;
wherein R5 and R6 together can constitute an heterocycle, the heterocycle can include one or more heteroatom from N, O and S;

as well as its racemic forms, tautomers, enantiomers, diastereomers, epimers and polymorphs, and mixtures thereof, and the pharmaceutically acceptable salts thereof.

In another preferred embodiment, the invention provides pyrazinone derivatives of formula (I), wherein:
n=0, 1, 2;
R1 is selected from:
hydrogen, alkyl, cycloalkyl, cycloalkylalkyl;
wherein alkyl, aryl, cycloalkyls and heteroaryl groups can be optionally substituted by one or more substituents selected from Y; preferably, R1 is: methyl, ethyl, propyl, butyl; each of these groups can be optionally substituted by one or more groups selected from Y;
R2 is an hydrogen;
R3 is selected from:
hydrogen, halogen, alkyl, aryl, heteroaryl;
wherein alkyl, aryl, cycloalkyls and heteroaryl groups can be optionally substituted by one or more substituents selected from Y; preferably, R3 is:
Cl, Br, phenyl optionally substituted by one or more groups selected from Y;
R4 is selected from:
  Z, wherein Z is:
alkyl, arylalkyl, aryloxyalkyl, arylalkoxyalkyl, heteroarylalkyl, heteroaryloxyalkyl, heteroarylalkoxyalkyl, heterocycloalkyl, heterocycloalkylalkyl, heterocycloalkyloxyalkyl, heterocycloalkylalkoxyalkyl, cycloalkyl, cycloalkylalkyl, cycloalkyloxyalkyl, cycloalkylalkoxyalkyl;
wherein the alkyl, aryl, heteroaryl, cycloalkyls and heterocycloalkyls groups can be optionally substituted by one or more substituents selected from Y;
heteroaryl and heterocycloalkyl groups can include one or more heteroatom from N, O and S;

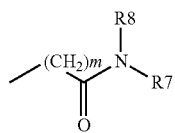

wherein:
m=1-6;
R7 and R8 are independently selected from:
hydrogen, aryl, heteroaryl, Z;
wherein aryl and heteroaryl groups can be optionally substituted by one or more substituents selected from Y;
R7 and R8 together can constitute an heterocycle; the heterocycle can include one or more heteroatom from N, O and S;

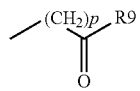

wherein:
p=1-6;
R9 is selected from:
aryl, heteroaryl, O—R10, Z;
wherein aryl and heteroaryl groups can be optionally substituted by one or more substituents selected from Y;
R10 is selected from:
hydrogen, alkyl, aryl, arylalkyl;
wherein alkyl, aryl, arylalkyl groups can be optionally substituted by one or more substituents selected from Y; preferably, R4 is: benzyl, phenylethyl, phenoxyethyl, phenyl-2-oxoethyl, 2-oxo-2-piperidi-1-ylethyl, N-phenylacetamide, N-methyl-N-phenylacetamide, N-cyclohexyl-N-methylacetamide; each of these groups can be optionally substituted by one or more groups selected from Y;
Y is selected from:
hydroxy, thio, halogen, cyano, trifluoromethoxy, trifluoromethyl, carboxy, carboxy methyle, carboxyethyle, alkyle, alkoxy, alkylamino, aryl, aryl sulfonylalkyl, aryloxy, arylalkoxy, amino, NR5R6, azido, nitro, guanidino, amidino, phosphono, oxo, carbamoyle, alkylsulfonyl, alkylsulfinyl, alkylthio, two Y groups can form a mehylenedioxy;
wherein R5 and R6 are independently selected from hydrogen, Z, alkyl, aryl, arylalkyl, heteroaryl, heteroarylalkyl;
wherein alkyl, aryl and heteroaryl groups can be optionally substituted by one or more substituents selected from Y;
wherein R5 and R6 together can constitute an heterocycle, the heterocycle can include one or more heteroatom from N, O and S; preferably, Y is: halogen, trifluoromethyl, alkyl, alkoxy;

Other preferred compounds are compounds of general formula (I), wherein R4 is selected from:

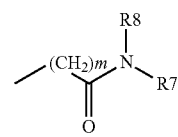

wherein m, R7 and R8 are as above defined;

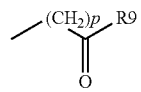

wherein p and R9 are as above defined;
as well as its racemic forms, tautomers, enantiomers, diastereomers, epimers and polymorphs, and mixtures thereof, and the pharmaceutically acceptable salts thereof.

The compounds of the formula (I) may be chosen from the following compounds:
3-(benzylthio)-1-ethylpyrazin-2(1H)-one
3-benzylsulfonyl-1-ethylpyrazin-2(1H)-one
3-[(4-chlorobenzyl)sulfonyl]-1-ethylpyrazin-2(1H)-one
3-[(4-methylbenzyl)sulfonyl]-1-propylpyrazin-2(1H)-one
3-[(4-fluorobenzyl)sulfonyl]-1-propylpyrazin-2(1H)-one
3-(benzylsulfonyl)-1-propylpyrazin-2(1H)-one
1-ethyl-3[(4-bromobenzyl)sulfonyl]pyrazin-2(1H)-one
3-[(4-chlorobenzyl)thio]-1-propylpyrazin-2(1H)-one
3-[(4-chlorobenzyl)sulfonyl]-1-propylpyrazin-2(1H)-one
3-[(3-Chlorobenzyl)sulfonyl]-1-propylpyrazin-2(1H)-one
1-methyl-3[(4-chlorobenzyl)sulfonyl]pyrazin-2(1H)-one
1-butyl-3-[(2-fluorobenzyl)sulfonyl]pyrazin-2(1H)-one
1-butyl-3-[(3-trifluoromethylbenzyl)sulfonyl]pyrazin-2(1H)-one
1-butyl-3-[(4-chlorobenzyl)sulfonyl]pyrazin-2(1H)-one
3-{[2-(4-chlorophenyl)ethyl]sulfonyl}-1-propylpyrazin-2(1H)-one
1-ethyl-3-{[2-(4-methoxyphenoxy)ethyl]sulfonyl}pyrazin-2(1H)-one
3-{[2-(4-chlorophenyl)-2-oxoethyl]sulfonyl}-ethylpyrazin-2(1H)-one
3-[1,1'-biphenyl-4-ylmethyl)sulfonyl]-1-ethylpyrazin-2(1H)-one 3-{[2-(4-chlorophenoxy)ethyl]sulfonyl}-1-ethylpyrazin-2(1H)-one
3-{[2-(4-methylphenyl)ethyl]sulfonyl}-1-propylpyrazin-2(1H)-one
3-{[2-(4-chlorophenyl)ethyl]sulfonyl}-1-ethylpyrazin-2(1H)-one
3-[(1,1'-biphenyl-4-ylmethyl)sulfonyl]-1-butylpyrazin-2(1H)-one
3-[(4-methoxybenzyl)sulfonyl]-1-propylpyrazin-2(1H)-one
3-[(3-Fluorobenzyl)sulfonyl]-1-methylpyrazin-2(1H)-one
3-[(2-Fluorobenzyl)sulfonyl]-1-methylpyrazin-2(1H)-one
1-Butyl-3-[(4-methoxybenzyl)sulfonyl]pyrazin-2(1H)-one
1-Ethyl-3-[(4-fluorobenzyl)sulfonyl]pyrazin-2(1H)-one
1-Ethyl-3-[(3-trifluoromethybenzyl)sulfonyl]pyrazin-2(1H)-one
1-Ethyl-3-[(3-fluorobenzyl)sulfonyl]pyrazin-2(1H)-one
1-Ethyl-3-[(2-fluorobenzyl)sulfonyl]pyrazin-2(1H)-one
1-Butyl-3-[(3-fluorobenzyl)sulfonyl]pyrazin-2(1H)-one
1-Butyl-3-[(2-methylbenzyl)sulfonyl]pyrazin-2(1H)-one
1-ethyl-3-[(2-methylbenzyl)sulfonyl]pyrazin-2(1H)-one
3-[(4-chlorobenzyl)sulfonyl]-1-ethylpyrazin-2(1H)-one
5-bromo-3-[(4-chlorobenzyl)thio]-1-ethylpyrazin-2(1H)-one
5-bromo-3-[(4-chlorobenzyl)sulfonyl]-1-ethylpyrazin-2(1H)-one
3-[(4-chlorobenzyl)sulfonyl]-1-ethyl-5-phenylpyrazin-2(1H)-one
3-[(4-chlorobenzyl)sulfonyl]-5-(4-chlorophenyl)-1-ethylpyrazin-2(1H)-one
3-[(4-chlorobenzyl)sulfonyl]-1-ethyl-5-(4-fluorophenyl)pyrazin-2(1H)-one
2-[(6-chloro-4-ethyl-3-oxo-3,4-dihydropyrazin-2-yl)thio]-N-phenyl acetamide
2-[(6-chloro-4-ethyl-3-oxo-3,4-dihydropyrazin-2-yl)sulfonyl]-N-phenylacetamide
5-chloro-1-ethyl-3-[(2-oxo-2-piperidin-1-ylethyl)sulfonyl]pyrazin-2(1H)-one
2-[(6-chloro-4-ethyl-3-oxo-3,4-dihydropyrazin-2-yl)sulfonyl]-N-methyl-N-phenylacetamide
2-[(6-chloro-4-ethyl-3-oxo-3,4-dihydropyrazin-2-yl)sulfonyl]-N-cyclohexyl-N-methylacetamide
as well as its racemic forms, tautomers, enantiomers, diastereomers, epimers and polymorphs, and mixtures thereof, and the pharmaceutically acceptable salts thereof.
as well as its racemic forms, tautomers, enantiomers, diastereomers, epimers and polymorphs, and mixtures thereof, and the pharmaceutically acceptable salts thereof.

More preferably, the compounds of the formula (I) according to the invention may be chosen from:
1-Ethyl-3-[(4-bromobenzyl)sulfonyl]pyrazin-2(1H)-one
1-Ethyl-3-benzylsulfonylpyrazin-2(1H)-one
1-Butyl-3-[(2-fluorobenzyl)sulfonyl]pyrazin-2(1H)-one
1-Butyl-3-[(3-trifluoromethylbenzyl)sulfonyl]pyrazin-2(1H)-one
1-Butyl-3-[(4-chlorobenzyl)sulfonyl]pyrazin-2(1H)-one
3-[(4-Chlorobenzyl)sulfonyl]-1-ethylpyrazin-2(1H)-one
3-[(4-Chlorobenzyl)sulfonyl]-1-propylpyrazin-2(1H)-one
3-[(4-Chlorobenzyl)sulfonyl]-5-(4-chlorophenyl)-1-ethylpyrazin-2(1H)-one
3-[(4-Fluorobenzyl)sulfonyl]-1-propylpyrazin-2(1H)-one
3-[(4-Methylbenzyl)sulfonyl]-1-propylpyrazin-2(1H)-one
3-{[2-(4-Chlorophenyl)ethyl]sulfonyl}-1-propylpyrazin-2(1H)-one
5-Chloro-1-ethyl-3-[(2-oxo-2-piperidin-1-ylethyl)sulfonyl]pyrazin-2(1H)-one
as well as its racemic forms, tautomers, enantiomers, diastereomers, epimers and polymorphs, and mixtures thereof, and the pharmaceutically acceptable salts thereof.

The invention also relates to the racemic forms, tautomeric forms, enantiomers, diastereoisomers, epimers and organic or mineral salts of the compounds of the general formula (I), as well as their crystalline forms, including their polymorphic forms and the polymorphic forms of the compounds of formula (I).

The present invention is directed not only to racemic mixtures of these compounds, but also to individual stereoisomers and/or diastereoisomers thereof, as well or as mixtures of these in all proportions.

The compounds of the invention of the formula (I), as defined above, containing a sufficiently acidic function or a sufficiently basic function, or both, may include the corresponding pharmaceutically acceptable salts of an organic or mineral acid, or of an organic or mineral base.

The expression "pharmaceutically acceptable salts" refers to the relatively non-toxic mineral and organic acid-addition salts, and the base-addition salts, of the compounds of the present invention. These salts may be prepared in situ during the final isolation and purification of the compounds.

In particular, the acid-addition salts may be prepared by separately reacting the purified compound in its purified form with an organic or mineral acid and isolating the salt thus formed. The resulting salts are, for example, hydrochlorides, hydrobromides, sulfates, hydrogenosulfates, dihydrogenophosphates, citrates, maleates, fumarates, trifluoroacetates, 2-naphtalenesulfonates, para-toluenesulfonates.

The invention also relates to pharmaceutically acceptable salts with organic or inorganic bases. In particular, the basic-addition salts may be prepared by separately reacting the purified compound in its purified form with an organic or inorganic base and isolating the salt thus formed. The resulting salts are, for example, metal salts, particularly alkali metal salts, alkaline-earth metal salts and transition metal salts (such as sodium, potassium, calcium, magnesium, aluminum), or salts obtained with bases, such as ammonia or secondary or tertiary amines (such as diethylamine, triethylamine, piperidine, piperazine, morpholine), or with basic amino-acids, or with osamines (such as meglumine), or with aminoalcohols (such as 3-aminobutanol and 2-aminoethanol).

The invention also relates to the salts used for chiral resolution of the racemates.

As examples, the following chiral acids can be used (+)-D-di-O-benzoyltartaric acid, (−)-L-di-O-benzoyltartaric acid, (−)-L-di-O,O'-p-toluyl-L-tartaric acid, (+)-D-di-O,O'-p-toluyl-L-tartaric acid, (R)-(+)-malic acid, (S)-(−)-malic acid, (+)-camphoric acid, (−)-camphoric acid, R-(−)1,1'-binaphtalen-2,2'-diyl hydrogenophosphonic, (+)-camphanic acid, (−)-camphanic acid, (S)-(+)-2-phenylpropionic acid, (R)-(+)-2-phenylpropionic acid, D-(−)-mandelic acid, L-(+)-mandelic acid, D-tartaric acid, L-tartaric acid, or any mixture of them.

As examples, the following chiral amines can be used: quinine, brucine, (S)-1-(benzyloxymethyl)propylamine (III), (−)-ephedrine, (4S,5R)-(+)-1,2,2,3,4-tetramethyl-5-phenyl-1,3-oxazolidine, (R)-1-phenyl-2-p-tolylethylamine, (S)-phenylglycinol, (−)-N-methylephedrine, (+)-(2S,3R)-4-dimethylamino-3-methyl-1,2-diphenyl-2-butanol, (S)-phenylglycinol, (S)-α-methylbenzylamine or any mixture of them.

Also included in the scope of the present invention are prodrugs of the compounds of formula (I).

The term "prodrug" as used herein refers to any compound that when administered to a biological system generates the "drug" substance (a biologically active compound) as a result of spontaneous chemical reaction(s), enzyme catalyzed chemical reaction(s), and/or metabolic chemical reaction(s).

In accordance with the present invention and as used herein, the following terms are defined with the following meanings, unless explicitly stated otherwise.

The term "aryl" refers to aromatic groups which have 5-14 ring atoms and at least one ring having a conjugated pi (π) electron system and includes biaryl groups, all of which may be optionally substituted. Suitable aryl groups include phenyl, naphthyl, biphenyl, anthryl, phenanthryl, indenyl and the like.

The term "heteroaryl" refers to 5-14 ring atom aromatic heterocycles containing 1 to 4 heteroatoms, as ring atoms in the aromatic ring and the remainder of the ring atoms being carbon atoms. Suitable heteroatoms include O, S, N. Suitable heteroaryl groups include furanyl, benzofuranyl, thienyl, pyridyl, pyridyl-N-oxide, pyrimidinyl, pyrazinyl, oxazolyl, thiazolyl, isoxazolyl, quinolinyl, triazolyl, pyridazinyl, pyrrolyl, imidazolyl, indazolyl, isothiazolyl, indolyl, oxadiazolyl and the like.

The term "cycloalkyl" means saturated carbocyclic rings, optionally substituted, and includes mono-, bi- and tri-cyclic compounds with 3 to 10 carbon atoms. Suitable cycloalkyl groups are: cyclopropyl, cyclobutyl, cyclopentyl, cyclohexyl, cycloheptyl, cyclooctyl, cyclodecyl, adamantyl and the like.

The term "heterocycloalkyl" refers to optionally substituted monocyclic, bicyclic or tricyclic radicals, comprising one or more heteroatoms, preferably chosen from among O, S and N, optionally in the oxidized state (for S and N), and optionally one or more double bonds. At least one of the rings preferably comprises from 1 to 4 endocyclic heteroatoms, more preferably from 1 to 3 heteroatoms. Most preferably, the heterocycloalkyl (or simply "heterocyclic") radical comprises one or more rings, each having from 5 to 8 nodes. Examples of heterocyclic radicals are: morpholinyl, piperidinyl, piperazinyl, thiazolidinyl, oxazolidinyl, tetrahydrothienyl, dihydrofuranyl, tetrahydrofuranyl, pyrazolidinyl, 1,3-dioxolanyl, pyrrolidinyl, pyranyl, dihydropyranyl, isoxazolidinyl, imidazolyl, imidazolidinyl and the like.

The term "heterocycle" refers to optionally substituted monocyclic, bicyclic or tricyclic radicals, comprising one or more heteroatoms, preferably chosen from among O, S and N, optionally in the oxidized state (for S and N), and optionally one or more double bonds. At least one of the rings preferably comprises from 1 to 4 endocyclic heteroatoms, more preferably from 1 to 3 heteroatoms. Examples of heterocycle are: piperidine, morpholine, piperazine, pyrrolidine, thiazolidine, oxazolidine, pyrazolidine, isoxazolidine, imidazolidine;

The term "alkyl" refers to a saturated aliphatic groups, including straight chain and branched chain groups. Suitable alkyl groups, having 1 to 20 carbon atoms, include methyl, ethyl, propyl, isopropyl, butyl, sec-butyl, tert-butyl, pentyl, hexyl, octyl, decanoyl, dodecanoyl, hexadecyl, octadecyl groups and the like.

The term "alkenyl" refers to unsaturated groups comprising at least one carbon-carbon double bond, and includes straight chain, branched chain and cyclic groups. Suitable alkenyl groups, having 2 to 20 carbon atoms, include ethenyl, 2-propenyl, 2-butenyl, 3-butenyl, 2-pentenyl, 3-pentenyl, 4-pentenyl and the like.

The term "alkynyl" refers to unsaturated groups comprising at least one carbon-carbon triple bond and includes straight chain, branched chain and cyclic groups; and optionally includes at least one carbon-carbon double bond. Suitable alkynyl groups, having 2 to 20 carbon atoms, include ethynyl, 2-propynyl, 2-butynyl, 3-butynyl, 2-pentynyl, 3-pentynyl, 4-pentynyl and the like.

The term "arylalkyl" refers to an alkyl group, preferably an alkyl group having 1 to 20 carbon atoms, substituted with an aryl group. Suitable arylalkyl groups include benzyl, picolyl, and the like.

The term "arylalkenyl" refers to an alkenyl group, preferably an alkenyl group having 1 to 20 carbon atoms, substituted with an aryl group.

The term "arylalkynyl" refers to an alkynyl group, preferably an alkynyl group having 1 to 20 carbon atoms, substituted with an aryl group.

The term "alkoxy" refers to the group alk-O— wherein "alk" is an alkyl group.

The term "aryloxy" refers to the group aryl-O—.

The term "aryloxyalkyl" refers to an alkyl group substituted with an aryloxy group.

The term "arylalkoxyalkyl" refers to an alkyl group substituted with an arylalkoxy group.

The term "arylalkoxy" refers to the group aryl-Alk-O—, wherein "Alk" is an alkyl group.

The term "arylthioalkyl" refers to an alkyl group substituted with an arylthio group.

The term "alkylsulfinyl" refers to an alkyl-SO— group.

The term "alkylsulfonyl" refers to an alkyl-SO$_2$— group.

The term "aryl sulfonylalkyl" refers to an alkyl group substituted with an arylsulfonyl (aryl-SO$_2$—) group.

The term "arylalkylthioalkyl" refers to an alkyl group substituted with an arylalkylthio.

The term "heteroarylalkyl" refers to an alkyl group substituted with a heteroaryl group.

The term "heteroaryloxyalkyl" refers to an alkyl group substituted with a heteroaryloxy group.

The term "heteroarylalkoxyalkyl" refers to an alkyl group substituted with a heteroarylalkoxy group.

The term "heteroarylthioalkyl" refers to an alkyl group substituted with a heteroarylthio group.

The term "heteroarylalkylthioalkyl" refers to an alkyl group substituted with a heteroarylalkylthio group.

The term "heterocycloalkylalkyl" refers to an alkyl group substituted with a heterocycloalkyl group.

The term "heterocycloalkyloxyalkyl" refers to an alkyl group substituted with a heterocycloalkyloxy group.

The term "heterocycloalkylalkoxyalkyl" refers to an alkyl group substituted with a heterocycloalkylalkoxy group.

The term "heterocycloalkylthioalkyl" refers to an alkyl group substituted with a heterocycloalkylthio group.

The term "heterocycloalkylalkylthioalkyl" refers to an alkyl group substituted with a heterocycloalkylalkylthio group.

The term "cycloalkylalkyl" refers to an alkyl group substituted with a cycloalkyl group.

The term "cycloalkyloxyalkyl" refers to an alkyl group substituted with a cycloalkyloxy group.

The term "cycloalkylalkoxyalkyl" refers to an, alkyl group substituted with a cycloalkylalkoxy group.

The term "lower" referred to herein in connection with organic radicals or compounds respectively defines such as with up to and including 10, preferably up to and including 6, and advantageously 1 to 4 carbon atoms. Such groups may be straight, branched, or cyclic chain.

The terms "alkylthio" refers to the group alkyl-S—.

The term "cycloalkylthio" refers to the group cycloalkyl-S—.

The term "cycloalkylthioalkyl" refers to an alkyl group substituted with a cycloalkylthio group.

The term "cycloalkyialkylthioalkyl" refers to an alkyl group substituted with a cycloalkylalkylthio group.

The term "halogen" refers to a fluorine, bromine or chlorine atom.

The term "amidino" refers to —C(NR5)-NR5R6 where R5R6 are as defined above, all, except hydrogen, are optionally substituted.

The term "carbamoyl" refers to an unsubstituted aminocarbonyl group.

The invention's compounds according to formula (I) exhibit an hypoglycemic activity, and are useful in the treatment of pathologies associated with the syndrome of insulin resistance.

Insulin resistance is characterised by a reduction in the action of insulin (cf. "Presse Medicale", (1997), 26(14), 671-677) and is involved in many pathological conditions, such as diabetes and more particularly non-insulin-dependent diabetes (type II diabetes or NIDDM), dyslipidaemia, obesity, arterial hypertension, and also certain cardiac, microvascular and macrovascular complications, for instance atherosclerosis, retinopathy and neuropathy. In this respect, reference will be made, for Example, to *Diabetes*, 37, (1988), 1595-1607; *Journal of Diabetes and its complications*, 12, (1998), 110-119; *Horm. Res.*, 38, (1992), 28-32.

The invention also relates to pharmaceutical composition containing as active ingredient at least one compound of formula (I), as defined above, and/or a pharmaceutically acceptable salt thereof, in combination with one or several pharmaceutically acceptable carrier, adjuvant, diluent or excipient. A person skilled in the art is aware of a whole variety of such carrier, adjuvant, diluent or excipient compounds suitable to formulate a pharmaceutical composition.

The pharmaceutical compositions of the present invention can be administered by a variety of routes including oral, parenteral, intravenous, intramuscular, rectal, permucous or percutaneous.

They will thus be presented in the form of injectable solutions or suspensions or multi-dose bottles, in the form of plain or coated tablets, sugar-coated tablets, wafer capsules, gel capsules, pills, sachets, powders, suppositories or rectal capsules, solutions or suspensions, for percutaneous use in a polar solvent, or for permucous use.

The excipients that are suitable for such administrations are pharmaceutically acceptable excipients, such as cellulose or microcrystalline cellulose derivatives, alkaline-earth metal carbonates, magnesium phosphate, starches, modified starches, lactose and the like for solid forms.

For rectal use, cocoa butter or polyethylene glycol stearates are the preferred excipients.

For parenteral use, water, aqueous solutions, physiological saline and isotonic solutions are the vehicles most appropriately used.

For example, in the case of an oral administration, for example in the form of granules, tablets or coated tablets, pills, capsules, gel capsules, gels, cachets or powders, a suitable posology of the compounds is between about 0.1 mg/kg and about 100 mg/kg, preferably between about 0.5 mg/kg and about 50 mg/kg, more preferably between about 1 mg/kg and about 10 mg/kg and most preferably between about 2 mg/kg and about 5 mg/kg of body weight per day.

If representative body weights of 10 kg and 100 kg are considered, in order to illustrate the daily oral dosage range that can be used and as described above, suitable dosages of the compounds of the formula (I) will be between about 1-10 mg/per day and 1000-10000 mg/per day, preferably between about 5-50 mg/per day and 500-5000 mg/per day, more preferably between 10-100 mg and 100-1000 mg/per day and most preferably between 20-200 mg and 50-500 mg/per day.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

As noted above, formulations of the present invention suitable for oral administration may be presented as discrete units, such as capsules, cachets or tablets, each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

In the non-insulin-dependent diabetes, for the man, the hyperglycemia is the results of two main defects: an alteration of the insulin secretion and a reduction in the effectiveness of insulin at level of three sites to knowing the liver, the muscles and adipose tissue.

The present invention also relates to compound of general formula (I) as well as its racemic forms, tautomers, enantiomers, diastereomers, epimers and polymorphs, and mixtures thereof, and the pharmaceutically acceptable salts thereof, for the preparation of a medicament for the prevention and/or treatment of pathologies associated with hyperglycaemia; for the preparation of a medicament that induces insulin secretion in response of glucose concentration, preferably for the treatment of diabetes, more preferably for the prevention and/or treatment of type II diabetes and pathologies associated to metabolic disorders, hypercholesteremia, hyperlipidemia, which are increased by hyperinsulinemia and hyperglycemia; for the treatment of diseases chosen from diabetes related microvascular and macrovascular complications, such as arterial hypertension, inflammatory processes, microangiopathy, macroangiopathy, retinopathy and neuropathy; for reducing hyperglycaemia, for the treatment of dyslipidaemia and obesity; or diseases such as cardiovascular diseases, comprising atherosclerosis, myocardial ischemia.

The present invention also relates to the use of at least a compound of the general formula (I), as well as its racemic forms, tautomers, enantiomers, diastereomers, epimers and polymorphs, and mixtures thereof, and the pharmaceutically acceptable salts, and pro-drugs thereof, for the prevention and/or treatment of pathologies associated with hyperglycaemia, preferably for the treatment of diabetes, more preferably for the prevention and/or treatment of type II diabetes and pathologies associated to metabolic disorders, hypercholesteremia, hyperlipidemia, which are increased by hyperinsulinemia and hyperglycemia; for the treatment of diseases chosen from diabetes related microvascular and macrovascular complications, such as arterial hypertension, inflammatory processes, microangiopathy, macroangiopathy, retinopathy and neuropathy; for reducing hyperglycaemia, for the treatment of dyslipidaemia and obesity; or diseases such as cardiovascular diseases, comprising atherosclerosis, myocardial ischemia.

The present invention also relates to manufacturing process of compounds of formula (I), as defined above, according to the following representative methods shown in Scheme 1 (Preparation of the intermediates pyrazinone derivatives); Scheme 2 (Preparation of pyrazinone derivatives, Method A)

or Scheme 3 (Preparation of pyrazinone derivatives, Method B), in which n, R1, R2, R3 and R4 are as above defined in formula (I).

The following schemes are given for representative purposes, and solely for the purpose of facilitating the representation. Needless to say, depending on the nature of the compounds of the formula (I) to be obtained, the methodologies presented may be adapted by a person skilled in the art by selecting the appropriate starting materials, in which the nature of the substituents R1, R4 may be modified, especially as a function of the nature and length of the desired chain.

The compounds useful according to the invention may be prepared, unless specifically specified, by the application or adaptation of known methods, by which are meant methods used heretofore or described in the literature, patents or patent applications, the Chemical Abstracts and on the Internet.

The compounds useful according to the invention may be prepared, unless specifically specified, by the application or adaptation of known methods, by which are meant methods used heretofore or described in the literature, patents or patent applications, the Chemical Abstracts and on the Internet.

Preparation of the Intermediates Pyrazinone Derivatives.

Scheme 1

(1)

(2)

(3)

in which R1 is as above defined in formula (I).

Compounds (2) are prepared by reacting diethyloxalate (1) with an amine in the presence of a quaternary ammonium salt, such as aliquat 336, in an inert solvent, such as chloroform, toluene or dichloromethane, at a temperature between 20° C. and the reflux, for 24 to 100 h.

Intermediates (3) with a side chain containing a protected aldehyde in the form of an acetal are prepared by reacting compounds of formula (2) with a protected aminoacetaldehyde dialkylacetate, such as (2,2-dimethoxyethyl)amine. The reaction is carried out in a solvent, such as an alcohol, for example 2-propanol, at a temperature between 20° C. and the reflux, for 1 to 24 h.

Pyrazinones (4) can be prepared by cyclization of compound (3) under acidic conditions, for example in a solvent, such as acetic acid, and catalytic amount of concentrated hydrochloric acid, at a temperature between 20° C. and the reflux, for 1 to 24 h.

Preparation of Pyrazinone Derivatives. Method a

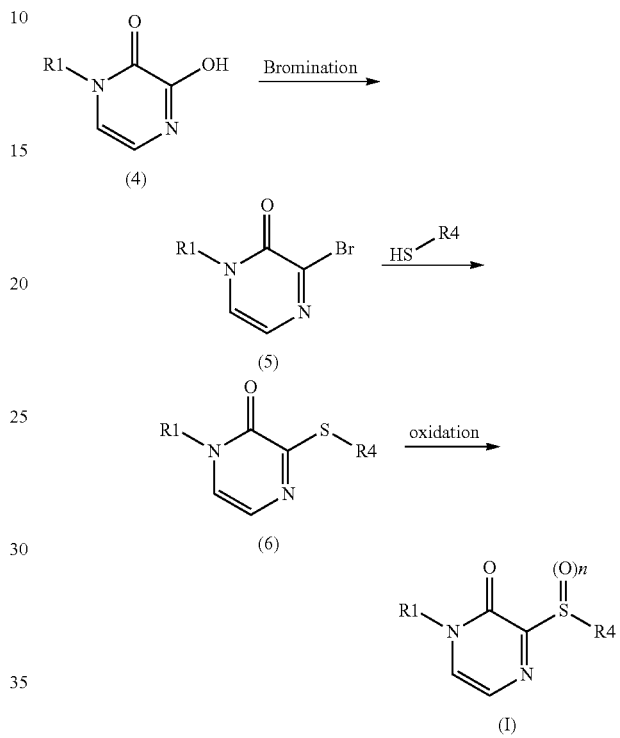

Scheme 2 in which n, R1 and R4 are as above defined in formula (I).

3-bromopyrazinones (5) are prepared by bromination of the corresponding 3-hydroxypyrazinones (4) using a brominating agent, such as $POBr_3$, in an inert solvent, such as 1,2-dichloroethane, at a temperature between 20° C. and the reflux, more preferably reflux, for 1 to 24 h.

Thio derivatives (I), wherein n=0, are prepared in reacting the 3-bromopyrazinones (5) with suitable thiols, such as, in a non limitative manner, benzylthiols, alkylthiols derivatives, optionally substituted, in the presence of at least one equivalent of an inorganic base, such as sodium or potassium carbonate, cesium carbonate, or an organic base, such as triethylamine or diisopropylethylamine in a solvent such as acetonitrile, tetrahydrofurane or toluene at a temperature between 20° C. and the reflux for 1 to 24 h.

Sulfone derivatives (I), wherein n=2 are prepared from compounds (I), wherein n=0 in using oxidizing agents, such as metachloro perbenzoic acid (MCPBA). Other preferred method uses at least one equivalent of potassium peroxymonosulfate (axone), in the presence of a base, such as sodium hydrogenocarbonate, in a solvent, such as tetrahydrofurane and water, at a temperature between −20° C. and reflux, preferably at room temperature, for 1 to 24 h.

Sulfinyl derivative (I), wherein n=1 are prepared from compounds (I), wherein n=0 using one equivalent of oxone, in the presence of a base, such as sodium hydrogenocarbonate, in a solvent, such as tetrahydrofurane and water, at a temperature between −20° C. and reflux, preferably at room temperature, for 1 to 4 h.

Preparation of Pyrazinone Derivatives. Method B

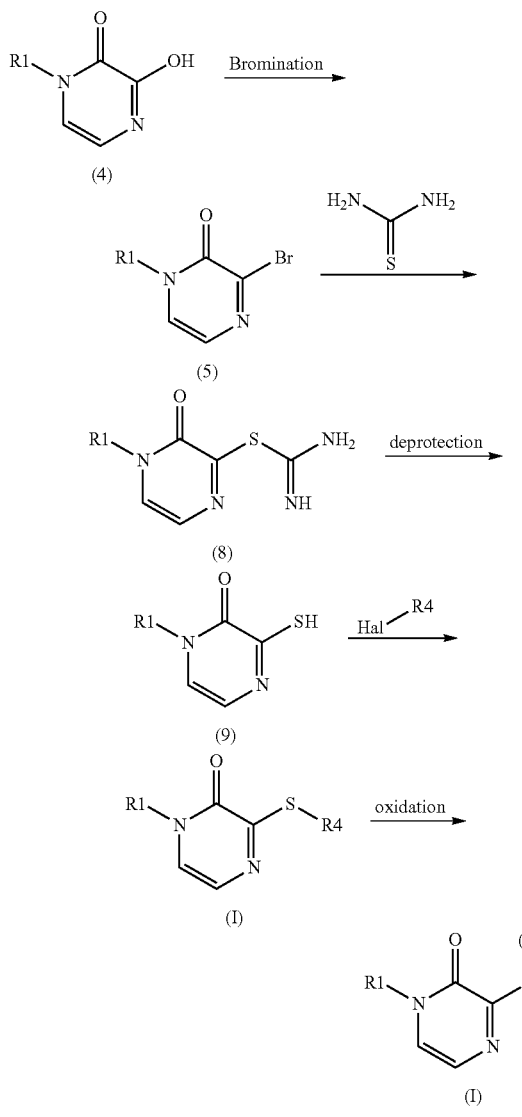

in which n, R1 and R4 are as above defined in formula (I).

3-bromopyrazinones (5) are prepared by bromination of the corresponding 3-hydroxypyrazinones (4) using a brominating agent, such as $POBr_3$, in an inert solvent, such as 1,2-dichloroethane, at a temperature between 20° C. and the reflux, more preferably reflux, for 1 to 24 h. Imidothiocarbamates (8) are prepared in reacting 3-bromopyrazinones (5) with thiourea in solvent, such as acetonitrile, methanol or ethanol, at a temperature between 20° C. and the reflux, preferably at room temperature, for 1 to 24 h. Imidothiocarbamates (8) are then hydrolyzed in the presence of a base, such as sodium or potassium hydroxide, to give the corresponding 3-mercaptopyrazinones (9). Compounds (I), wherein n=0, are prepared in reacting 3-mercaptopyrazinones (9) with halogeno-R4 such as, in a non limitative manner, optionally substituted benzyl bromides, in the presence of at least one equivalent of an inorganic base, such as sodium or potassium carbonate, cesium carbonate, or an organic base, such as triethylamine or diisopropylethylamine, in a solvent, such as dichloromethane, acetonitrile, dimethylformamide, tetrahydrofurane, dioxane or toluene, at a temperature between 20° C. and the reflux, for 1 to 24 h.

Sulfone derivatives (I), wherein n=2, are prepared from compounds (I), wherein n=0, in using oxidizing agents, such as MCPBA.

Other preferred method uses at least one equivalent of oxone, in the presence of a base, such as sodium hydrogenocarbonate, in a solvent, such as tetrahydrofurane and water, at a temperature between −20° C. and reflux, preferably at room temperature, for 1 to 24 h.

Sulfinyl derivative (I), wherein n=1 are prepared from compounds (I), wherein n=0 using one equivalent of oxone, in the presence of a base, such as sodium hydrogenocarbonate, in a solvent, such as tetrahydrofurane and water, at a temperature between −20° C. and reflux, preferably at room temperature, for 1 to 4 h.

The examples that follow illustrate the invention without, however, limiting it. The starting materials used are known products or products prepared according to known procedures. The percentages are expressed on a weight basis, unless otherwise mentioned.

The compounds were characterised especially via the following analytical techniques.

The NMR spectra were acquired using a Bruker Avance DPX 300 MHz NMR spectrometer.

The masses were determined by HPLC coupled to an Agilent Series 1100 mass detector. The melting points (m.p.) were measured on a Stuart Scientific.

EXAMPLES

Example 1 ethyl(ethylamino)(oxo)acetate

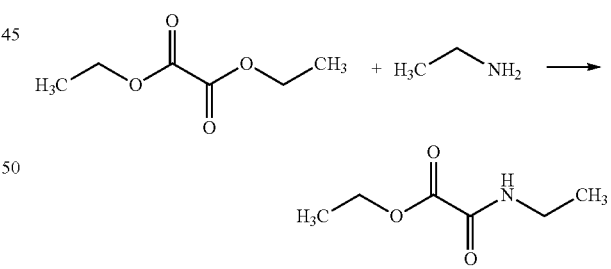

To 135.8 ml (1000 mM) of diethyloxalate and 1 g of aliquat 336 in 1000 ml of dichloromethane were added 64.4 ml (1000 mM) of ethylamine (70% in water). The reaction mixture was stirred at room temperature for 72 h. The reaction mixture was dried over anhydrous sodium sulfate and the solvent was removed under vacuum, to give an oil, wick was further purified by silica gel column chromatography, using dichloromethane/dimethylketone (95/5) as eluant, to give 59.9 g of ethyl(ethyl amino)(oxo)acetate as an oil. Yield: 41.3%.

NMR $^1$H (300 MHz/DMSO-d6) δ (ppm): 1.06 (t, 3H), 1.28 (t, 3H), 3.17 (m, 2H), 4.22 (q, 2H), 8.92 (s, 1H)

Example 2

N-(2,2-dimethoxyethyl)-N'-ethylethanediamide

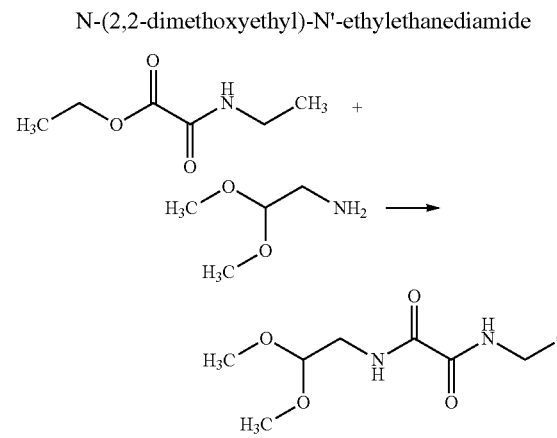

59.9 g (412.6 mM) of ethyl(ethylamino)(oxo)acetate and 45 ml (412.6 mM) of (2,2-dimethoxyethyl)amine in 480 ml of 2-propanol were stirred at room temperature for 16 h. A white precipitate was filtered, washed with 2-propanol and dried under vacuum, to give 67.8 g of N-(2,2-dimethoxyethyl)-N'-ethylethanediamide. Yield: 80.5%.

NMR $^1$H (300 MHz/DMSO-d6) δ (ppm): 1.07 (t, 3H), 3.15 (m, 2H), 3.27 (m, 8H), 4.51 (m, 1H), 8.62 (m, 1H), 8.81 (m, 1H)

Example 3

1-ethyl-3-hydroxypyrazine-2(1H)-one

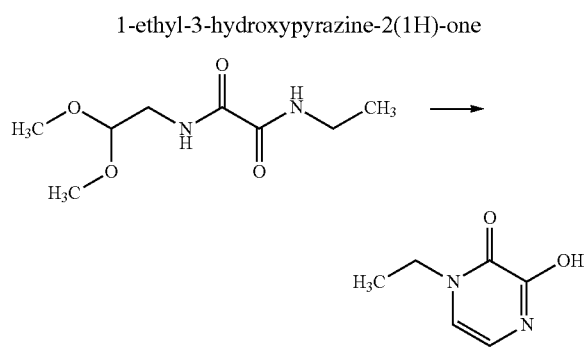

67.5 g (330 mM) of N-(2,2-dimethoxyethyl)-N'-ethylethanediamide and 2 ml of concentrated hydrochloric acid in 390 ml of acetic acid were refluxed under stirring for 1 h. The solvent was removed under vacuum to give an oil, which was further purified by silica gel column chromatography, using dichloromethane/methanol (95/5) as eluant to give 37 g of 1-ethyl-3-hydroxy pyrazine-2(1H)-one, as an oil. Yield: 79.5%.

NMR $^1$H (300 MHz/DMSO-d6) δ (ppm): 1.20 (t, 3H), 3.73 (q, 2H), 6.34 (d, 1H), 6.56 (d, 1H), 11.22 (s, 1H)

Method A

Example 4

3-promo-1-ethylpyrazin-2(1H)-one

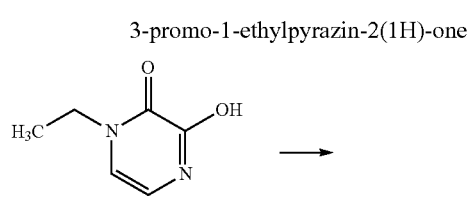

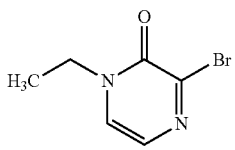

10.5 g (75 mM) of 1-ethyl-3-hydroxypyrazine-2(1H)-one and 23.1 g (80.5 mM) of phosphorous oxybromide in 75 ml of dichloroethane were refluxed under stirring for 2 h. The reaction mixture was then neutralized to pH 7-8 with a saturated aqueous solution of sodium carbonate, while maintaining the temperature at 10° C. The reaction mixture was then stirred at room temperature for 1 h. Water was added and the organic phase was extracted with dichloromethane. The combined organic layer was washed with water, dried on anhydrous sodium sulfate and the solvent was removed under vacuum. The compound was further purified by silica gel column chromatography, using dichloromethane as eluant, to give 6.1 g of 3-bromo-1-ethylpyrazin-2(1H)-one as a solid. Yield: 40.2%.

NMR $^1$H (300 MHz/DMSO-d6) δ (ppm): 1.18 (t, 3H), 3.87 (q, 2H), 7.13 (d, 1H), 7.75 (d, 1H)

The following compounds were obtained using the same procedure as in Example 4.

Example 4-2

3-bromo-1-methylpyrazin-2(1H)-one

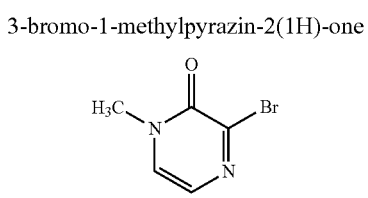

NMR $^1$H (300 MHz/DMSO-d6) δ (ppm): 3.51 (s, 3H), 7.18 (d, 1H), 7.80 (d, 1H)

Example 4-3

3-bromo-1-butylpyrazin-2(1H)-one

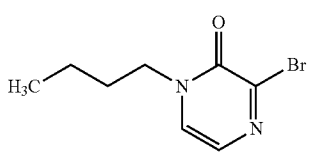

NMR $^1$H (300 MHz/DMSO-d6) δ (ppm): 0.90 (t, 3H), 1.30 (m, 2H), 1.65 (m, 2H), 3.93 (t, 2H), 7.20 (d, 1H), 7.79 (d, 1H)

Example 4-4

3-bromo-1-propylpyrazin-2(1H)-one

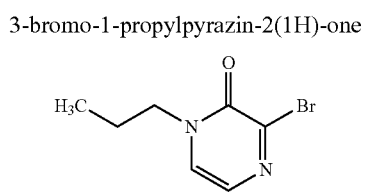

$C_7H_9BrN_2O$=217.06 Mass 218.0 (M+1)

Example 5

3-(benzylthio)-1-ethylpyrazin-2(1H)-one

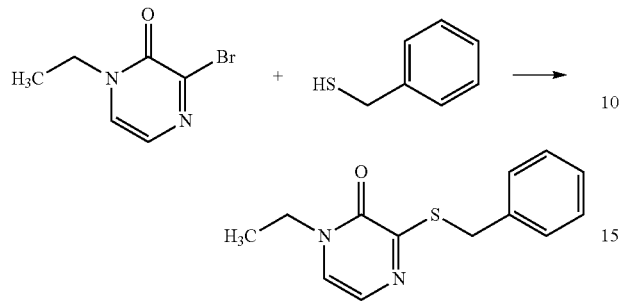

To 250 mg (1.23 mM) of 3-bromo-1-ethylpyrazin-2(1H)-one and 340.3 mg (2.46 mM) of potassium carbonate in 4 ml of THF were added 159 μl (1.35 mM) of benzylthiol. The reaction mixture was then stirred at room temperature for 16 h. Water was added and the organic phase was extracted with ethyle acetate. The combined organic layer was washed with water, dried on anhydrous sodium sulfate and the solvent was removed under vacuum, to give a solid, which was triturated in diisopropyle oxide, filtrated and dried under vacuum, to give 250 mg of 3-(benzylthio)-1-ethylpyrazin-2(1H)-one. Yield: 82%.

NMR $^1$H (300 MHz/DMSO-d6) δ (ppm): 1.24 (t, 3H), 3.92 (q, 2H), 4.26 (s, 2H), 7.31 (m, 4H), 7.39 (d, 2H), 7.49 (d, 1H)

Example 6

3-benzylsulfonyl-1-ethylpyrazin-2(1H)-one

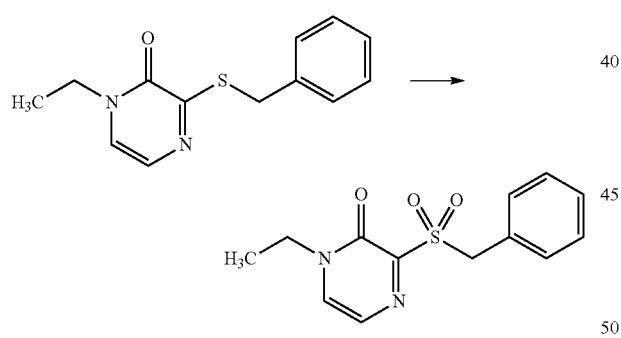

To 177 mg (0.72 mM) of 3-(benzylthio)-1-ethylpyrazin-2 (1H)-one and 66.4 mg (0.79 mM) of sodium hydrogenocarbonate in 4 ml of tetrahydrofurane were added 1.67 g (2.87 mM) of potassium peroxymonosulfate (oxone) in 4 ml of water. The reaction mixture was then stirred at room temperature for 16 h. Water was added and the organic phase was extracted twice with ethyle acetate. The combined organic layer was washed with water, dried on anhydrous sodium sulfate and the solvent was removed under vacuum, to give a solid, which was triturated in diisopropyle oxide, filtrated and dried under vacuum, to give 103 mg of 3-benzylsulfonyl-1-ethylpyrazin-2(1H)-one. Yield: 52%.

NMR $^1$H (300 MHz/DMSO-d6) δ (ppm): 1.34 (t, 3H), 4.10 (q, 2H), 4.91 (s, 2H), 7.34 (m, 5H), 7.57 (d, 1H), 8.22 (d, 1H)

The following compounds were obtained using the same procedure as in Example 6.

Example 6-2

3-[(4-chlorobenzyl)sulfonyl]-1-ethylpyrazin-2(1H)-one

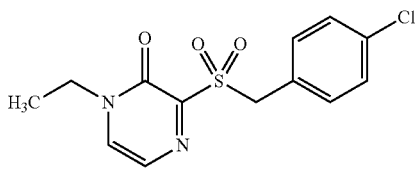 [SMILES: CCn1ccnc(S(=O)(=O)Cc2ccc(Cl)cc2)c1=O]

$C_{13}H_{13}ClN_2O_3S$=312.77 Mass 313.0 (M+1)
m.p.: 115-118° C.

Example 6-3

3-[(4-methylbenzyl)sulfonyl]-1-propylpyrazin-2(1H)-one

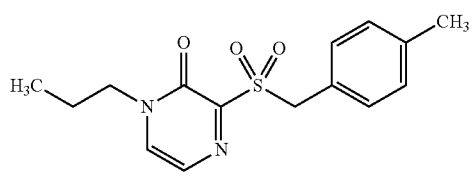 [SMILES: CCCn1ccnc(S(=O)(=O)Cc2ccc(C)cc2)c1=O]

$C_{15}H_{18}N_2O_3S$=306.38 Mass 307.1 (M+1)
m.p.: 128-130° C.

Example 6-4

3-[(4-fluorobenzyl)sulfonyl]-1-propylpyrazin-2(1H)-one

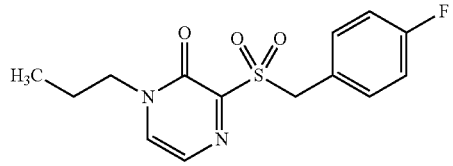 [SMILES: CCCn1ccnc(S(=O)(=O)Cc2ccc(F)cc2)c1=O]

$C_{14}H_{15}FN_2O_3S$=310.34 Mass 311.1 (M+1)
m.p.: 123-125° C.

Example 6-5

3-(benzylsulfonyl)-1-propylpyrazin-2(1H)-one

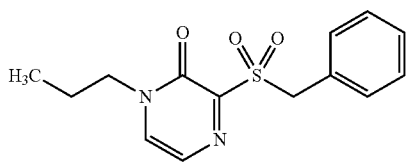 [SMILES: CCCn1ccnc(S(=O)(=O)Cc2ccccc2)c1=O]

$C_{14}H_{16}N_2O_3S$=292.35 Mass 293.1 (M+1)
m.p.: 133-135° C.

Example 6-6

1-ethyl-3-[(4-bromobenzyl)sulfonyl]pyrazin-2(1H)-one

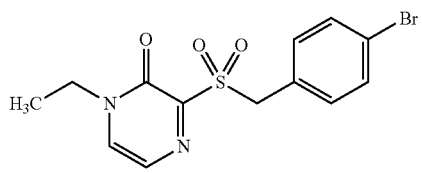 [SMILES: CCn1ccnc(S(=O)(=O)Cc2ccc(Br)cc2)c1=O]

$C_{13}H_{13}BrN_2O_3S=357.22$ Mass 357.0 (M+1)
m.p.: 135-138° C.

Method B

Example 7

3-oxo-4-propyl-3,4-dihydropyrazin-2-yl imidothiocarbamate hydrobromide

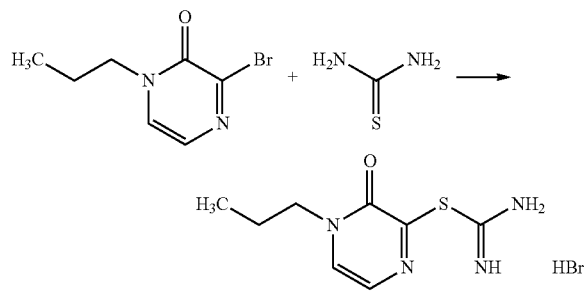

25.4 g (117 mM) of 3-bromo-1-propylpyrazin-2(1H)-one and 8.9 g (117 mM) of thiourea in 120 ml of ethanol were stirred at room temperature for 2 h. A precipitate is filtrated, washed with ethanol and dried under vacuum, to give 26.8 of 3-oxo-4-propyl-3,4-dihydropyrazin-2-yl imidothiocarbamate as its hydrobromide. Yield: 78.1%.

NMR $^1$H (300 MHz/DMSO-d6) δ (ppm): 0.88 (t, 3H), 1.71 (m, 2H), 3.92 (t, 2H), 7.46 (s, 1H), 7.88 (s, 1H), 9.44 (m, 2H), 9.81 (s, 2H)

The following compounds were obtained using the same procedure as in Example 7

Example 7-2

4-ethyl-3-oxo-3,4-dihydropyrazin-2-yl imidothiocarbamate

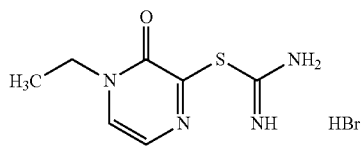

Free base $C_7H_{10}N_4OS=198.25$ Mass 199.0 (M+1)
m.p.: 175-177° C.

Example 7-3

4-methyl-3-oxo-3,4-dihydropyrazin-2-yl imidothiocarbamate

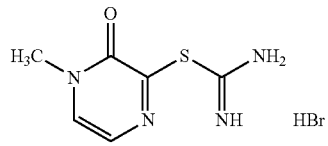

NMR $^1$H (300 MHz/DMSO-d6) δ (ppm): 3.5 (s, 3H), 7.40 (d, 1H), 7.87 (d, 1H), 9.40 (s, 2H), 9.78 (s, 2H)

Example 7-4

4-butyl-3-oxo-3,4-dihydropyrazin-2-yl imidothiocarbamate

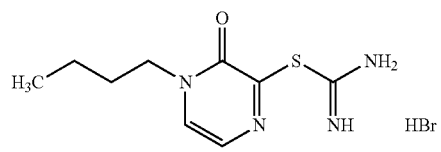

NMR $^1$H (300 MHz/DMSO-d6) δ (ppm): 0.89 (t, 3H), 1.30 (m, 2H), 1.65 (m, 2H), 3.95 (t, 2H), 7.46 (d, 1H), 7.91 (d, 1H), 9.46 (s, 2H), 9.83 (s, 2H)

Example 8

3-mercapto-1-propylpyrazin-2(1H)-one

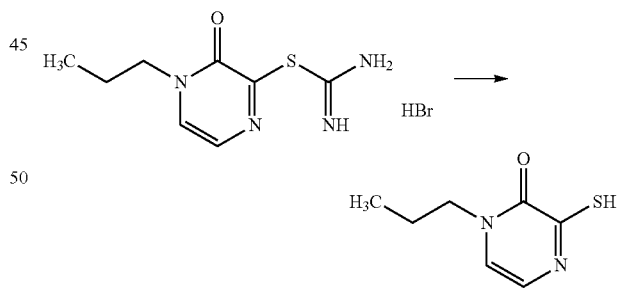

26.7 g (91.3 mM) of 3-oxo-4-propyl-3,4-dihydropyrazin-2-yl imidothiocarbamate hydrobromide in 25 ml of a 3N solution of aqueous sodium hydroxide were stirred at room temperature for 3 h. The reaction mixture was neutralized with HCl 3N and the precipitate was filtered, washed with water and dried under vacuum, to give 9.7 g of 3-mercapto-1-propylpyrazin-2(1H)-one as a yellow solid. Yield: 62.3%.

NMR $^1$H (300 MHz/DMSO-d6) δ (ppm): 0.86 (t, 3H), 1.62 (m, 2H), 3.72 (t, 2H), 6.5 (d, 1H), 7.07 (d, 1H), 13.46 (s, 1H)

The following compounds were obtained using the same procedure as in Example 8.

Example 8-2

3-mercapto-1-butylpyrazin-2(1H)-one

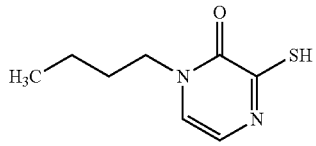

NMR $^1$H (300 MHz/DMSO-d6) δ (ppm): 0.89 (t, 3H), 1.26 (m, 2H), 1.59 (m, 2H), 3.75 (t, 2H), 6.53 (d, 1H), 7.08 (d, 1H), 13.45 (s, 1H)
m.p.: 141-143° C.

Example 8-3

3-mercapto-1-methylpyrazin-2(1H)-one

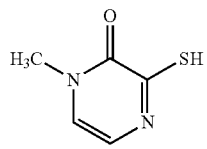

NMR $^1$H (300 MHz/DMSO-d6) δ (ppm): 3.30 (s, 3H), 6.52 (d, 1H), 7.02 (d, 1H), 13.41 (s, 1H)

Example 8-4

3-mercapto-1-ethylpyrazin-2(1H)-one

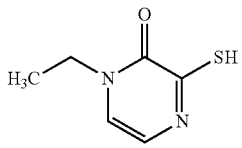

$C_8H_8N_2OS$=156.21 Mass 157.0 (M+1)
m.p.: 165-170° C.

Example 9

3-[(4-chlorobenzyl)thio]-1-propylpyrazin-2(1H)-one

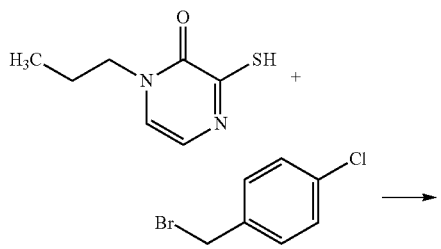

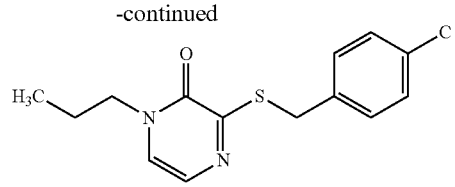

500 mg (2.30 mM) of 3-mercapto-1-propylpyrazin-2(1H)-one, 319.2 µl (1.21 mM) of 4-chlorobenzylbromide and 637 mg (4.6 mM) of potassium carbonate in 4 ml of tetrahydrofurane were stirred overnight at room temperature. Water was added and the aqueous layer was extracted with ethyle acetate. The organic layer was separated and washed with water, dried on anhydrous sodium sulfate and evaporated under vacuum, to give an oil which was purified by silica gel column chromatography, using dichloromethane/dimethylketone (98/2) as eluant, to give 600 mg of 3-[(4-chlorobenzyl)thio]-1-propylpyrazin-2(1H)-one. Yield: 88%.

NMR $^1$H (300 MHz/DMSO-d6) δ (ppm): 0.83 (t, 3H), 1.63 (m, 2H), 3.80 (t, 2H), 4.23 (s, 2H), 7.27 (d, 1H), 7.36 (m, 4H), 7.43 (d, 1H)

Example 10

3-[(4-chlorobenzyl)sulfonyl]-1-propylpyrazin-2(1H)-one

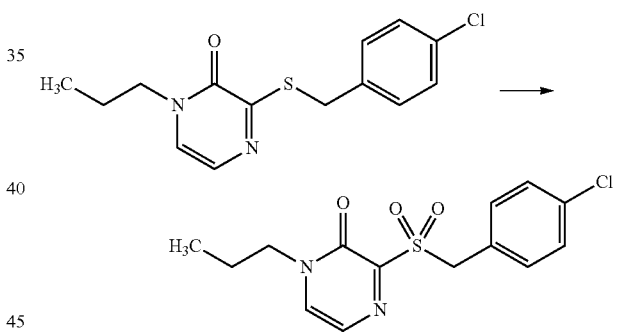

To 360 mg (1.17 mM) of 3-[(4-chlorobenzyl)thio]-1-propylpyrazin-2(1H)-one and 107.7 mg (1.28 mM) of sodium hydrogenocarbonate in 2 ml of tetrahydrofurane were added 2.9 g (4.7 mM) of oxone in 2 ml of water. The reaction mixture was stirred for 3 h at room temperature. Water was added and the aqueous layer was extracted with ethyle acetate. The organic layer was separated and washed with water, dried on anhydrous sodium sulfate and evaporated under vacuum. The residue was taken up in diisopropyle oxide, filtered and washed with diisopropyle oxide, to give 90 mg of 3-[(4-chlorobenzyl)sulfonyl]-1-propylpyrazin-2(1H)-one. Yield: 23%.

NMR $^1$H (300 MHz/DMSO-d6) δ (ppm): 0.90 (t, 3H), 1.75 (m, 2H), 4.02 (t, 2H), 4.93 (s, 2H), 7.34 (d, 2H), 7.41 (d, 2H), 7.58 (d, 1H), 8.24 (d, 1H)

$C_{14}H_{15}ClN_2O_3S$=326.8 Mass 327.0 (M+1)
M.P.: 125-128° C.

The following compounds were obtained using the same procedure as in Example 10.

Example 10-2

1-methyl-3-[(4-chlorobenzyl)sulfonyl]pyrazin-2(1H)-one

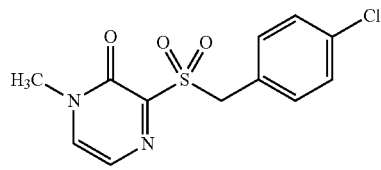 [SMILES: Cn1ccnc(S(=O)(=O)Cc2ccc(Cl)cc2)c1=O]

$C_{12}H_{11}ClN_2O_3S$=298.75 Mass 299.0 (M+1)

Example 10-3

1-butyl-3-[(2-fluorobenzyl)sulfonyl]pyrazin-2(1H)-one

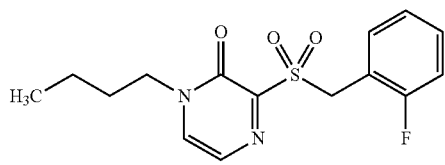 [SMILES: CCCCn1ccnc(S(=O)(=O)Cc2ccccc2F)c1=O]

$C_{15}H_{17}FN_2O_3S$=324.37 Mass 325.1 (M+1)

Example 10-4

1-butyl-3-[(3-trifluoromethylbenzyl)sulfonyl]pyrazin-2(1H)-one

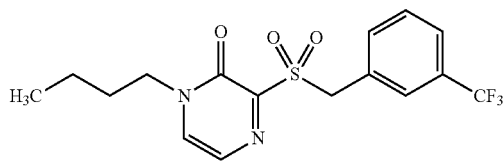 [SMILES: CCCCn1ccnc(S(=O)(=O)Cc2cccc(C(F)(F)F)c2)c1=O]

$C_{16}H_{17}F_3N_2O_3S$=374.38 Mass 375.1 (M+1)

Example 10-5

1-butyl-3-[(4-chlorobenzyl)sulfonyl]pyrazin-2(1H)-one

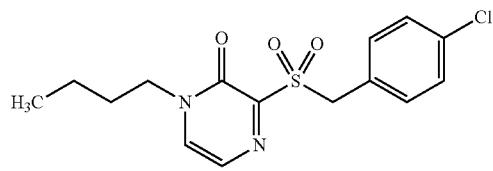 [SMILES: CCCCn1ccnc(S(=O)(=O)Cc2ccc(Cl)cc2)c1=O]

$C_{15}H_{17}ClN_2O_3S$=340.83 Mass 341.0 (M+1)

Example 10-6

3-{[2-(4-chlorophenyl)ethyl]sulfonyl}-1-propylpyrazin-2(1H)-one

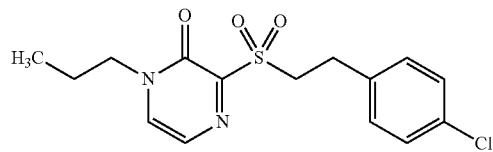 [SMILES: CCCn1ccnc(S(=O)(=O)CCc2ccc(Cl)cc2)c1=O]

$C_{15}H_{17}ClN_2O_3S$=340.83 Mass 341.1 (M+1)

Example 10-7

1-ethyl-3-{[2-(4-methoxyphenoxy)ethyl]sulfonyl}pyrazin-2(1H)-one

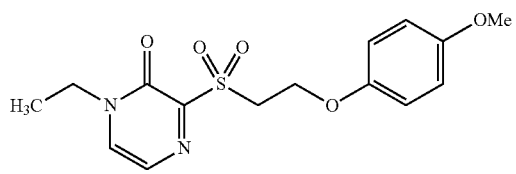 [SMILES: CCn1ccnc(S(=O)(=O)CCOc2ccc(OC)cc2)c1=O]

$C_{15}H_{18}N_2O_5S$=338.38 Mass 339.1 (M+1)
m.p.: 100-103° C.

Example 10-8

3-{[2-(4-chlorophenyl)-2-oxoethyl]sulfonyl}-1-ethylpyrazin-2(1H)-one

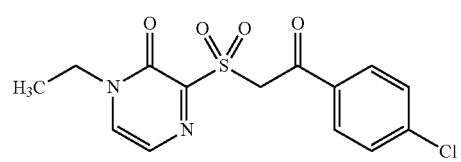 [SMILES: CCn1ccnc(S(=O)(=O)CC(=O)c2ccc(Cl)cc2)c1=O]

$C_{14}H_{13}ClN_2O_4S$=340.78 Mass 341.0 (M+1)

Using the same procedure as in Example 10, with one equivalent of potassium peroxymonosulfate (oxone), the following compound was synthesized:

Example 10-9

3-[(4-chlorobenzyl)sulfinyl]-1-ethylpyrazin-2(1H)-one

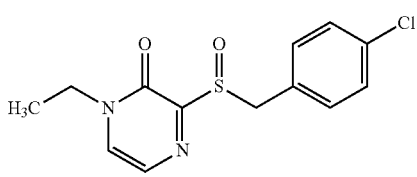 [SMILES: CCn1ccnc(S(=O)Cc2ccc(Cl)cc2)c1=O]

$C_{13}H_{13}ClN_2O_2S$=296.77 Mass 297.0 (M+1)

Example 10-10

3-[(1,1'-biphenyl-4-ylmethyl)sulfonyl]-1-ethylpyrazin-2(1H)-one

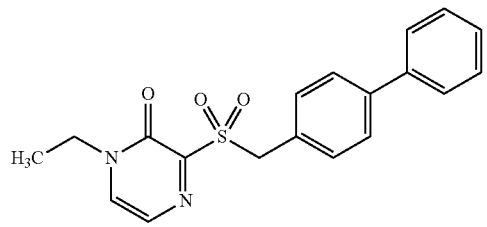 [SMILES: CCn1ccnc(S(=O)(=O)Cc2ccc(-c3ccccc3)cc2)c1=O]

C$_{19}$H$_{18}$N$_2$O$_3$S=354.42 Mass 355.1 (M+1)

Example 10-11

3-{[2-(4-chlorophenoxy)ethyl]sulfonyl}-1-ethylpyrazin-2(1H)-one

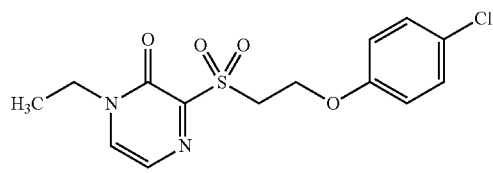 [SMILES: CCn1ccnc(S(=O)(=O)CCOc2ccc(Cl)cc2)c1=O]

C$_{14}$H$_{15}$ClN$_2$O$_3$S=342.80 Mass 343.0 (M+1)

Example 10-12

3-{[2-(4-methylphenyl)ethyl]sulfonyl}-1-propylpyrazin-2(1H)-one

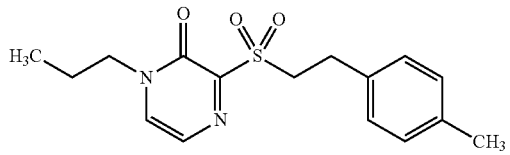 [SMILES: CCCn1ccnc(S(=O)(=O)CCc2ccc(C)cc2)c1=O]

C$_{16}$H$_{20}$N$_2$O$_3$S=320.41 Mass 321.1 (M+1)

Example 10-13

3-{[2-(4-chlorophenyl)ethyl]sulfonyl}-1-ethylpyrazin-2(1H)-one

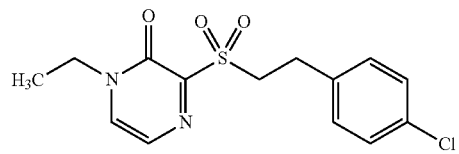 [SMILES: CCn1ccnc(S(=O)(=O)CCc2ccc(Cl)cc2)c1=O]

C$_{14}$H$_{15}$ClN$_2$O$_3$S=326.80 Mass 327.1 (M+1)

Example 10-14

3-[(1,1'-biphenyl-4-ylmethyl)sulfonyl]-1-butylpyrazin-2(1H)-one

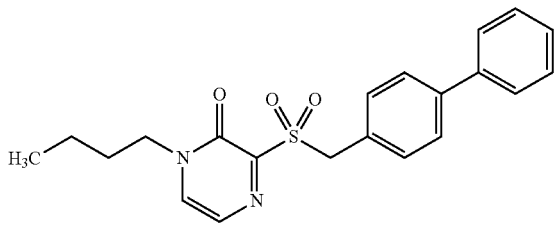 [SMILES: CCCCn1ccnc(S(=O)(=O)Cc2ccc(-c3ccccc3)cc2)c1=O]

C$_{21}$H$_{22}$N$_2$O$_3$S=382.48 Mass 383.1 (M+1)

Example 10-15

3-[(4-methoxybenzyl)sulfonyl]-1-propylpyrazin-2(1H)-one

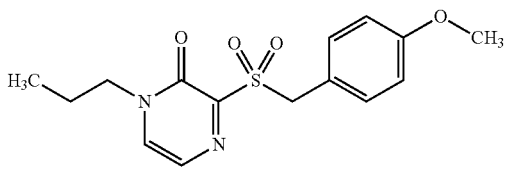 [SMILES: CCCn1ccnc(S(=O)(=O)Cc2ccc(OC)cc2)c1=O]

C$_{15}$H$_{13}$N$_2$O$_4$S=322.38 Mass 323.1 (M+1)

Example 10-16

3-[(3-Fluorobenzyl)sulfonyl]-1-methylpyrazin-2(1H)-one

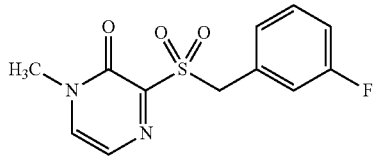 [SMILES: Cn1ccnc(S(=O)(=O)Cc2cccc(F)c2)c1=O]

C$_{12}$H$_{11}$FN$_2$O$_3$S=282.29 Mass 283.0 (M+1)

Example 10-17

3-[(3-Chlorobenzyl)sulfonyl]-1-propylpyrazin-2(1H)-one

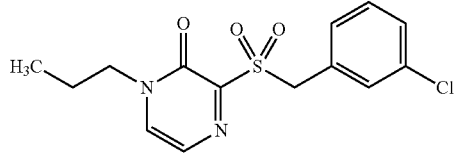 [SMILES: CCCn1ccnc(S(=O)(=O)Cc2cccc(Cl)c2)c1=O]

C$_{14}$H$_{15}$ClN$_2$O$_3$S=326.80 Mass 327.0 (M+1)

Example 10-18

3-[(2-Fluorobenzyl)sulfonyl]-1-methylpyrazin-2(1H)-one

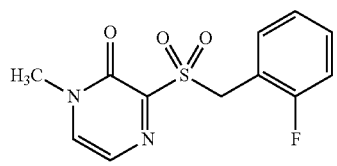 [SMILES: Cn1ccnc(S(=O)(=O)Cc2ccccc2F)c1=O]

C₁₂H₁₁FN₂O₃S=282.29 Mass 283.0 (M+1)

Example 10-19

1-Butyl-3-[(4-methoxybenzyl)sulfonyl]pyrazin-2(1H)-one

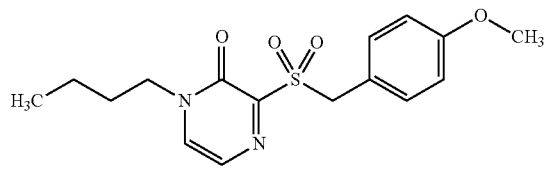 [SMILES: CCCCn1ccnc(S(=O)(=O)Cc2ccc(OC)cc2)c1=O]

C₁₆H₂₀N₂O₄S=336.41 Mass 337.1 (M+1)

Example 10-20

1-Ethyl-3-[(4-fluorobenzyl)sulfonyl]pyrazin-2(1H)-one

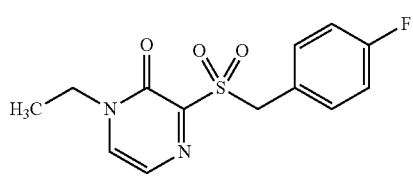 [SMILES: CCn1ccnc(S(=O)(=O)Cc2ccc(F)cc2)c1=O]

C₁₃H₁₃FN₂O₃S=296.32 Mass 297.1 (M+1)

Example 10-21

1-Ethyl-3-[(3-trifluoromethybenzyl)sulfonyl]pyrazin-2(1H)-one

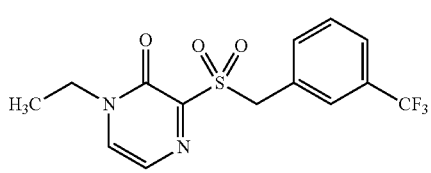 [SMILES: CCn1ccnc(S(=O)(=O)Cc2cccc(C(F)(F)F)c2)c1=O]

C₁₄H₁₃F₃N₂O₃S=346.33 Mass 347.1 (M+1)

Example 10-22

1-Ethyl-3-[(3-fluorobenzyl)sulfonyl]pyrazin-2(1H)-one

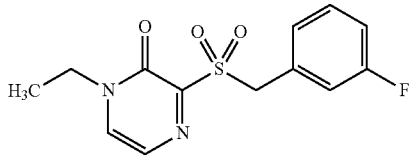 [SMILES: CCn1ccnc(S(=O)(=O)Cc2cccc(F)c2)c1=O]

C₁₃H₁₃FN₂O₃S=296.32 Mass 297.1 (M+1)

Example 10-23

1-Ethyl-3-[(2-fluorobenzyl)sulfonyl]pyrazin-2(1H)-one

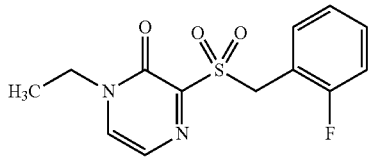 [SMILES: CCn1ccnc(S(=O)(=O)Cc2ccccc2F)c1=O]

C₁₃H₁₃FN₂O₃S=296.32 Mass 297.0 (M+1)

Example 10-24

1-Butyl-3-[(3-fluorobenzyl)sulfonyl]pyrazin-2(1H)-one

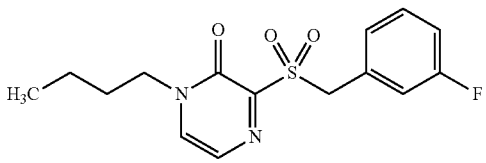 [SMILES: CCCCn1ccnc(S(=O)(=O)Cc2cccc(F)c2)c1=O]

C₁₅H₁₇FN₂O₃S=324.37 Mass 325.1 (M+1)

Example 10-25

1-Butyl-3-[(2-methylbenzyl)sulfonyl]pyrazin-2(1H)-one

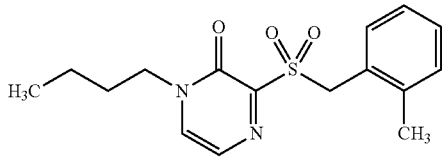

C₁₆H₂₀N₂O₃S=320.41 Mass 321.1 (M+1)

Example 10-26

1-ethyl-3-[(2-methylbenzyl)sulfonyl]pyrazin-2(1H)-one

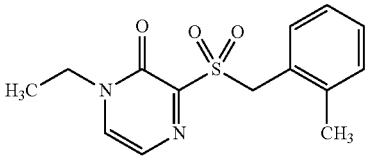 [SMILES: CCn1ccnc(S(=O)(=O)Cc2ccccc2C)c1=O]

C₁₄H₁₆N₂O₃S=292.35 Mass 293.0 (M+1)

Example 11

3,5-dibromo-1-ethylpyrazin-2(1H)-one

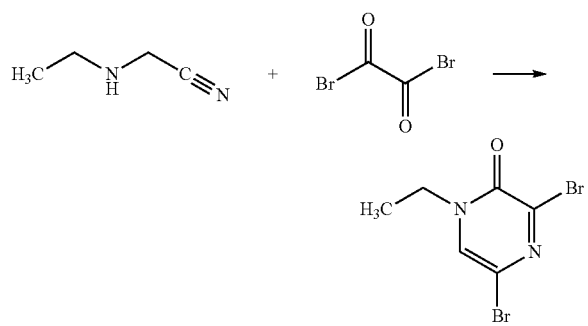

To 35 g (290 mM) of ethylaminoacetonitrile hydrochloride in 500 ml of dichloromethane were added 40.9 ml (435 mM) of oxalyl bromide. The reaction mixture was refluxed for 20 h under stirring. The solvent was removed under vacuum and the residue was further purified by silica gel column chromatography, using dichloromethane as eluant, to give 10 g of 3,5-dibromo-1-ethylpyrazin-2(1H)-one as a white solid. Yield: 12.2%.

NMR $^1$H (300 MHz/DMSO-d6) δ (ppm): 1.26 (t, 3H), 3.92 (q, 2H), 8.20 (s, 1H)

The following compounds were obtained using the same procedure as in Example 11.

Example 11-2

3,5-dichloro-1-ethylpyrazin-2(1H)-one

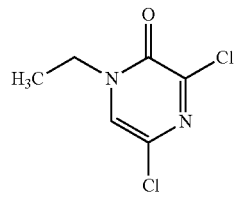

NMR $^1$H (300 MHz/DMSO-d6) δ (ppm: 1.03 (t, 3H), 3.72 (q, 2H), 7.92 (s, 1H), 7.80 (d, 1H)

$C_6H_6Cl_2N_2O$=193.03 Mass 193.0 (M+1)

Example 12

5-bromo-3-[(4-chlorobenzyl)thio]-1-ethylpyrazin-2(1H)-one

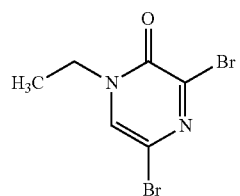

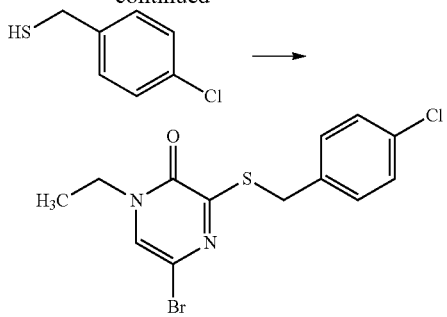

5 g (17.7 mM) of 3,5-dibromo-1-ethylpyrazin-2(1H)-one, 2.34 ml (17.7 mM) of 4-chlorobenzylthiol and 4.9 g (35.5 mM) of potassium carbonate in 40 ml of tetrahydrofurane were stirred for 4 h at room temperature. 100 ml of water were added and the so obtained precipitate was filtered, washed with water and dried, to give 4.8 g of 5-bromo-3-[(4-chlorobenzyl)thio]-1-ethylpyrazin-2(1H)-one as a solid. Yield: 75.4%.

$C_{13}H_{12}BrClN_2OS$=359.67 Mass 359.7 (M+1)

Example 13

5-bromo-3-[(4-chlorobenzyl)sulfonyl]-1-ethylpyrazin-2(1H)-one

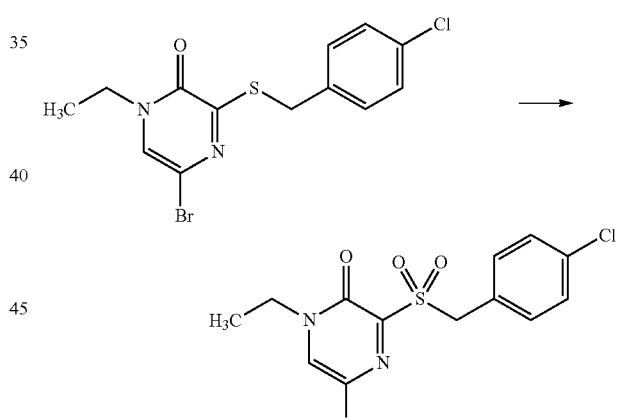

4.6 g (12.7 mM) of 5-bromo-3-[(4-chlorobenzyl)thio]-1-ethylpyrazin-2(1H)-one and 9.9 g (40 mM) of metachloroperbenzoic acid (70%) in 75 ml of dichloromethane were stirred for 10 min at room temperature. Aqueous 2M solution of sodium metabisulphite was added, the organic layer was separated and washed with an aqueous solution of hydrogenocarbonate, then with water and evaporated under vacuum. The residue was taken up in diisopropyle oxide. A solid was filtered and washed with diisopropyle oxide, to give 4.3 g of 5-bromo-3-[(4-chlorobenzyl)sulfonyl]-1-ethylpyrazin-2(1H)-one. Yield: 87%.

NMR $^1$H (300 MHz/DMSO-d6) δ (ppm): 1.31 (t, 3H), 4.01 (q, 2H), 4.89 (s, 2H), 7.35 (d, 2H), 7.42 (d, 2H), 8.61 (s, 1H)

m.p.: 145-147° C.

$C_{13}H_{12}BrClN_2O_3S$=391.67 Mass 392.9 (M+1)

Example 14

3-[(4-chlorobenzyl)sulfonyl]-1-ethyl-5-phenylpyrazin-2(1H) one

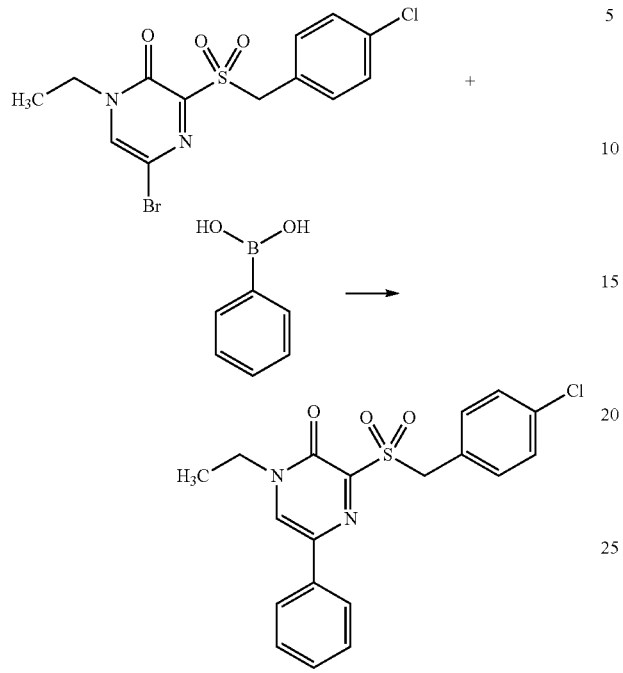

200 mg (0.51 mM) of 5-bromo-3-[(4-chlorobenzyl)sulfonyl]-1-ethylpyrazin-2(1H)-one and 20 mg of tetrakis Pd(PPh3) in 4 ml of toluene were stirred for 10 min at room temperature under nitrogen atmosphere. 93.4 mg (0.77 mM) of phenyl boronic acid and 1.5 ml of a 2M cesium carbonate aqueous solution were added and the reaction mixture was refluxed under stirring for 1 h30. 10 ml of water and 10 ml of toluene were added, the organic layer was separated. The aqueous layer was extracted with toluene and the combined organic layer was separated and washed with water, dried on anhydrous sodium sulfate and concentrated under vacuum. The residue was further purified by silica gel column chromatography, using dichloromethane/dimethylketone (95/5) as eluant, to give 52 mg of 3-[(4-chlorobenzyl)sulfonyl]-1-ethyl-5-phenylpyrazin-2(1H)-one as a solid. Yield: 26%.

NMR $^1$H (300 MHz/DMSO-d6) δ (ppm): 1.38 (t, 3H), 4.13 (q, 2H), 5.00 (s, 2H), 7.41 (m, 7H), 7.83 (d, 2H), 8.84 (s, 1H)
m.p.: 146-148° C.
$C_{19}H_{17}ClN_2O_3S$=388.87 Mass 389.0 (M+1)

Example 14-2

3-[(4-chlorobenzyl)sulfonyl]-5-(4-chlorophenyl)-1-ethylpyrazin-2(1H)-one

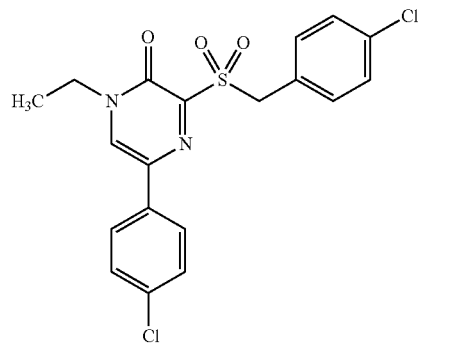 [SMILES: CCn1cc(-c2ccc(F)cc2)nc(S(=O)(=O)Cc2ccc(Cl)cc2)c1=O]

$C_{19}H_{16}Cl_2N_2O_3S$=423.31 Mass 423.0 (M+1)

Example 14-3

3-[(4-chlorobenzyl)sulfonyl]-1-ethyl-5-(4-fluorophenyl)pyrazin-2(1H)-one

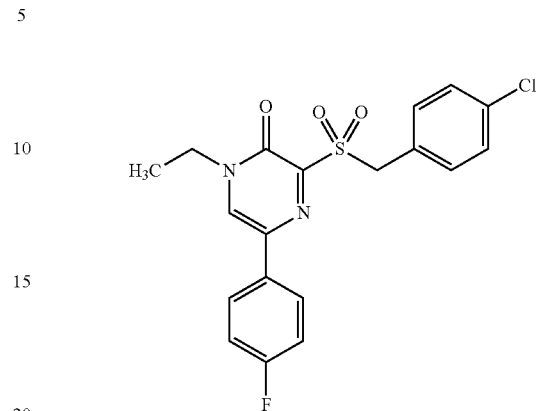

$C_{19}H_{16}ClFN_2O_3S$=406.86 Mass 407.0 (M+1)

Example 15

6-chloro-4-ethyl-3-oxo-3,4-dihydropyrazin-2-yl-imidothiocarbamate hydrochloride

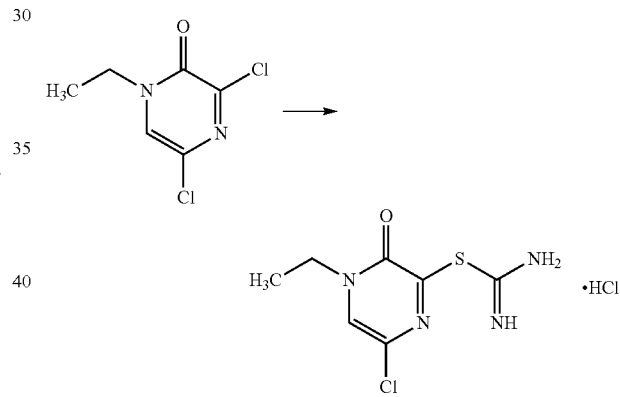

5 g (25.9 mM) of 3,5-dichloro-1-ethylpyrazin-2(1H)-one and 2 g (26 mM) of thiourea in 50 ml of ethanol were stirred for 4 h at room temperature. The solvent was removed under vacuum and the residue was taken up in acetonitrile, to give 4.7 g of 6-chloro-4-ethyl-3-oxo-3,4-dihydropyrazin-2-yl-imidothiocarbamate hydrochloride as a solid. Yield: 67.4%.
free base $C_7H_9ClN_4OS$=234.7 Mass 233.0 (M−1)

Example 16

5-chloro-1-ethyl-3-mercaptopyrazin-2(1H)-one

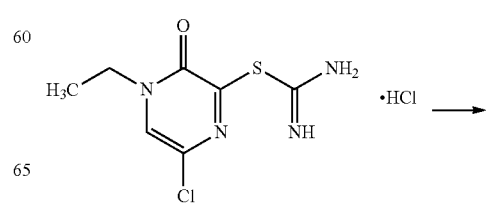

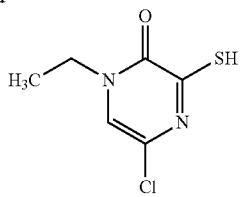

4.6 g (17.5 mM) of 6-chloro-4-ethyl-3-oxo-3,4-dihydropyrazin-2-yl-imidothiocarbamate hydrochloride in 25 ml of a 3N solution of aqueous sodium hydroxide were stirred at 65° C. for 1 h. The reaction mixture was neutralized with aqueous 3N hydrochloric acid, and the so obtained precipitate was filtered, to give 2.7 g of 5-chloro-1-ethyl-3-mercaptopyrazin-2(1H)-one as a yellow solid. Yield: 81%.

$C_6H_7ClN_2OS$=190.65 Mass 188.9 (M−1)
m.p.: 142-144° C.

Example 17

2-[(6-chloro-4-ethyl-3-oxo-3,4-dihydropyrazin-2-yl)thio]-N-phenylacetamide

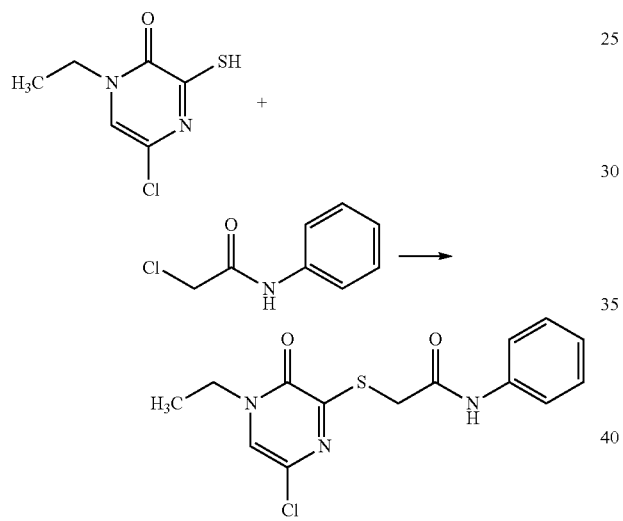

200 mg (1.05 mM) of 5-chloro-1-ethyl-3-mercaptopyrazin-2(1H)-one, 178 mg (1 mM) of 2-chloro-N-phenylacetamide and 135.6 mg (1.05 mM) of diisopropylethylamine in 5 ml of tetrahydrofurane were stirred overnight at room temperature. Water was added and the precipitate was filtered and washed with water, to give 170 mg of 2-[(6-chloro-4-ethyl-3-oxo-3,4-dihydropyrazin-2-yl)thio]-N-phenylacetamide. Yield: 50%.

$C_{14}H_{14}ClN_3O_2S$=323.8 Mass 324.0 (M+1)
m.p.: 156-158° C.

Example 18

2-[(6-chloro-4-ethyl-3-oxo-3,4-dihydropyrazin-2-yl)sulfonyl]-N-phenylacetamide

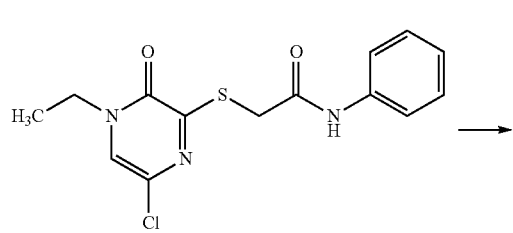

To 100 mg (031 mM) of 2-[(6-chloro-4-ethyl-3-oxo-3,4-dihydropyrazin-2-yl)thio]-N-phenylacetamide and 26 mg (0.31 mM) of sodium hydrogenocarbonate in 2 ml of tetrahydrofurane were added 760 mg (1 mM) of oxone in 2 ml of water.

The reaction mixture was stirred overnight at room temperature. Water was added and the precipitate was filtered and washed with water, to give 55 mg of 2-[(6-chloro-4-ethyl-3-oxo-3,4-dihydropyrazin-2-yl)sulfonyl]-N-phenylacetamide as a solid. Yield: 50%.

NMR $^1$H (300 MHz/DMSO-d6) δ (ppm): 1.30 (t, 3H), 4.05 (q, 2H), 4.71 (s, 2H), 7.11 (m, 1H), 7.30 (t, 2H), 7.46 (d, 2H); 8.60 (s, 1H), 10.49 (s, 1H)
m.p.: 178-180° C.

Example 18-2

5-chloro-1-ethyl-3-[(2-oxo-2-piperidin-1-ylethyl)sulfonyl]pyrazin-2(1H)-one

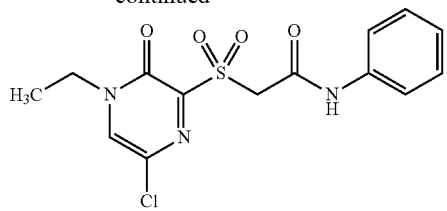

$C_{13}H_{18}ClN_3O_4S$=347.82 Mass 348.0 (M+1)

Example 18-3

2-[(6-chloro-4-ethyl-3-oxo-3,4-dihydropyrazin-2-yl)sulfonyl]-N-methyl-N-phenylacetamide

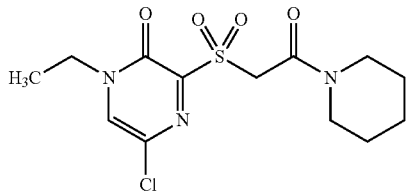 [SMILES: CCn1cc(Cl)nc(S(=O)(=O)CC(=O)N2CCCCC2)c1=O]

$C_{15}H_{16}ClN_3O_4S$=369.82 Mass 370.0 (M+1)

Example 18-4

2-[(6-chloro-4-ethyl-3-oxo-3,4-dihydropyrazin-2-yl)sulfonyl]-N-cyclohexyl-N-methylacetamide

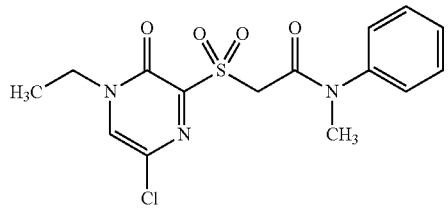 [SMILES: CCn1cc(Cl)nc(S(=O)(=O)CC(=O)N(C)c2ccccc2)c1=O]

$C_{15}H_{22}ClN_3O_4S$=375.87 Mass 376.1 (M+1)

Biological Assays

The INS-1 cells were selected to evaluate compounds of the present invention for their superior response to glucose and other physiological and pharmacological insulin secretagogues.

Culture of Pancreatic INS-1 Cells

INS-1 cells were cultured in complete medium, RPMI1640 containing 1 mM sodium pyruvate, 50 μM 2-mercaptoethanol, 2 mM glutamine, 10 mM HEPES, 100 IU/mL penicillin, and 100 μg/mL streptomycin (CM), supplemented with 10 mM glucose, and 10% (vol/vol) heat-inactivated fetal calf serum (FCS), as described by Asfari et al. (Endocrinology 130: 167-178, 1992).

Insulin Secretion Assay

INS-1 cells were plated and cultured in 48-well plates. After 2 days of culture, the medium was removed and cells were cultured for 24 h with a medium change to 5 mM glucose, 1% FCS. The cells were then washed with Krebs-Ringer Bicarbonate HEPES buffer (KRBH; 135 mM NaCl; 3.6 mM KCl; 5 mM NaHCO3; 0.5 mM NaH2PO4; 0.5 mM MgCl2; 1.5 mM CaCl2 and 10 mM HEPES; pH 7.4) 0.1% BSA containing 2.8 mM glucose and preincubated for 30 min at 37° C. in the same buffer. The cells were then washed twice and incubated for 1 h in KRBH 0.1% BSA containing 4.2 mM glucose and different concentrations of the tested molecule. Insulin concentration in the collected supernatants was measured with ELISA using rat insulin antibody (Insulin Rat Elit PLUS, cat. ref 10-1145-01).

Insulin secretion results are expressed in % of control (glucose 4.2 mM).

Insulin Secretion in INS-1 Cells (Glucose at 4.2 mM)

| Example | % of ctrl at 10 μM | % of ctrl at 50 μM |
| --- | --- | --- |
| 6 | 128 | 184 |
| 6-2 | 142 | 276 |
| 6-3 | 144 | 207 |
| 6-4 | 142 | 203 |
| 6-6 | 164 | 362 |
| 10 | 155 | 331 |
| 10-3 | 108 | 236 |
| 10-4 | 187 | 272 |
| 10-5 | 153 | 261 |
| 10-6 | 127 | 180 |
| 14-2 | 181 | — |
| 18-2 | 159 | 213 |

Insulin Secretion in Diabetic NOSTZ Rat Islets.

Materials and Methods.

Islets Isolation and Treatments.

14±3 weeks non-fasted NOSTZ (PORTHA et al., 1974) male rats (Charles Rivers-Domaine des Oncins, l'Arbresle, France) were anesthetised with sodium pentobarbital (Nembutal®: 45 mg/kg in 5 ml/kg administered intra peritoneally) and body temperature was maintained with a heat lamp.

Rat pancreatic islets of Langerhans were isolated from the pancreas of 8 rats by collagenase P (Boehringer, Meylan, France) digestion. Islets were purified by sedimentation in Hanks balanced salt solution [NaCl (137 mM); KCl (5.36 mM); MgSO$_4$, 7 H$_2$O (0.81 mM); Na$_2$HPO$_4$, 12 H$_2$O (0.34 mM); KH$_2$PO$_4$ (0.44 mM); CaCl$_2$, 2 H$_2$O (1.26 mM); NaHCO$_3$ (4.17 mM)] followed by Ficoll gradient separation.

Islets were then hand-picked under stereoscopic microscope and batches of 3 islets were incubated for 90 minutes at 37° C. with continuous shaking under a humidified condition (95% O$_2$, 5% CO$_2$) in 1 ml of Krebs/Hepes pH 7 solution [NaCl (115 mM), NaHCO$_3$ (24 mM), KCl (5 mM), MgCl$_2$ (1 mM), CaCl$_2$, 2 H$_2$O (1 mM), 0.2% of Bovine serum albumin (Fraction V, fatty acid free, Boehringer, Mannheim), 10 mM Hepes] containing the required glucose or compound concentration.

Compounds were dissolved in DMSO at 2.10-2M stock solutions. They were then diluted at the required concentration in Krebs/Hepes buffer containing the required glucose concentration.

At the end of incubation, media was collected and insulin levels were measured using ELISA (EUROBIO, Courtaboeuf, France).

TABLE

Dose response effect of compounds on insulin secretion in diabetic NOSTZ rat islets.

| EXAMPLE (M) | GLUCOSE 2.8 MM | | GLUCOSE 8 MM | | | | |
| --- | --- | --- | --- | --- | --- | --- | --- |
| | 0 | 10 – 4 | 0 | 10 – 7 | 10 – 6 | 10 – 6 | 10 – 4 |
| 10 | 100 ± 5 | 178 ± 7 | 100 ± 5 | 84 ± 7 | 90 ± 4 | 133 ± 7 | 203 ± 11 |
| 6-3 | 100 ± 9 | 121 ± 7 | 100 ± 6 | 101 ± 6 | 108 ± 5 | 131 ± 5 | 271 ± 6 |

Islets were hand-picked and incubated in the presence of increasing concentrations of compounds in the presence of glucose at 2.8 or 8 mM. At the end of incubation, media was collected and insulin levels were measured using ELISA method. Results are expressed as % of glucose control (2.8 or 8 mM) and represent Means±SEM.

In islets isolated from N0STZ diabetic rats, the compounds showed no effect in the presence of a low, non-stimulatory, glucose concentration (2.8 mM), even at high concentration ($10^{-4}$ M), while they potentiated insulin secretion in response to 8 mM glucose, a stimulatory glucose concentration. These results show that the effect of the compounds on the insulin secretion is dependent on the glucose level and suggest that a treatment with these compounds should avoid hypoglycemic risk.

The invention claimed is:

1. A method for treating diabetes associated with lack of insulin production or for treating type II diabetes,
   comprising administering to a subject in need thereof an effective amount of a compound of formula (I), or a racemic form, tautomer, enantiomer, diastereomer, epimer or polymorph thereof, or a mixture thereof, or a pharmaceutically acceptable salt thereof

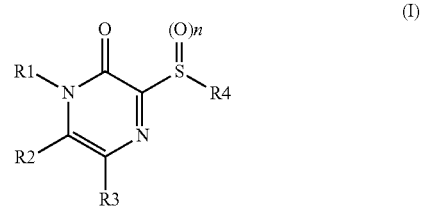

wherein n=0, 1, or 2;

R1 is alkyl, alkenyl, or alkynyl, which is optionally substituted by one or more substituents Y;

R2 is hydrogen, halogen, heteroaryl, or Z;

R3 is hydrogen, halogen, aryl, heteroaryl, or Z, wherein aryl and heteroaryl groups are optionally substituted by one or more substituents Y;

R4 is arylalkyl, aryloxyalkyl, arylalkoxyalkyl, arylthioalkyl, arylalkylthioalkyl, heteroaryl, heteroarylalkyl, heteroaryloxyalkyl, heteroarylalkoxyalkyl, heteroarylthioalkyl, heteroarylalkylthioalkyl, heterocycloalkyl, heterocycloalkyloxyalkyl, heterocycloalkylalkoxyalkyl, heterocycloalkylthioalkyl, heterocycloalkylalkylthioalkyl, arylalkenyl, arylalkynyl, cycloalkyl, cycloalkylalkyl, cycloalkyloxyalkyl, cycloalkylalkoxyalkyl, cycloalkylthioalkyl, or cycloalkylalkylthioalkyl, which is optionally substituted by one or more substituents Y, wherein heteroaryl and heterocycloalkyl groups include one or more heteroatoms each selected from the group consisting of N, O and S, or is

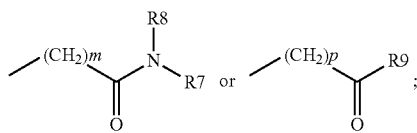

m=1-6;

R7 and R8 are each independently hydrogen, aryl, heteroaryl, or Z, wherein aryl and heteroaryl groups are optionally substituted by one or more substituents Y;

or

R7 and R8 together constitute a heterocycle, which includes one or more heteroatoms each selected from the group consisting of N, O and S;

p=1-6;

R9 is aryl, heteroaryl, O—R10, or Z, wherein aryl and heteroaryl groups are optionally substituted by one or more substituents Y;

R10 is hydrogen, alkyl, aryl, or arylalkyl, wherein alkyl, aryl, and arylalkyl groups are optionally substituted by one or more substituents Y;

Z is alkyl, alkenyl, alkynyl, aryl, arylalkyl, aryloxyalkyl, arylalkoxyalkyl, arylthioalkyl, arylalkylthioalkyl, heteroaryl, heteroarylalkyl, heteroaryloxyalkyl, heteroarylalkoxyalkyl, heteroarylthioalkyl, heteroarylalkylthioalkyl, heterocycloalkyl, heterocycloalkylalkyl, heterocycloalkyloxyalkyl, heterocycloalkylalkoxyalkyl, heterocycloalkylthioalkyl, heterocycloalkylalkylthioalkyl, arylalkenyl, arylalkynyl, cycloalkyl, cycloalkylalkyl, cycloalkyloxyalkyl, cycloalkylalkoxyalkyl, cycloalkylthioalkyl, or cycloalkylalkylthioalkyl, which is optionally substituted by one or more substituents Y, wherein heteroaryl and heterocycloalkyl groups include one or more heteroatoms each selected from the group consisting of N, O and S;

Y is hydroxy, halogen, cyano, trifluoromethoxy, trifluoromethyl, carboxy, carboxy methyl, carboxyethyl, alkyl, alkoxy, alkylamino, aryl, aryl sulfonylalkyl, aryloxy, arylalkoxy, amino, NR5R6, azido, nitro, guanidino, amidino, phosphono, carbamoyl, alkylsulfonyl, alkylsulfinyl, or alkylthio, or two Y groups form a methylenedioxy; and R5 and R6 are independently hydrogen, alkyl, aryl, arylalkyl, heteroaryl, or heteroarylalkyl, wherein alkyl, aryl and heteroaryl groups are optionally substituted by one or more substituents Y;

or

R5 and R6 together constitute a heterocycle; which includes one or more heteroatoms each selected from the group consisting of N, O and S.

2. A method according to claim 1, wherein in the compound of formula (I)

n=0, 1, or 2;

R1 is alkyl, which is optionally substituted by one or more substituents Y;

R2 is hydrogen, halogen, or alkyl, wherein alkyl groups are optionally substituted by one or more substituents Y;

R3 is hydrogen, halogen, alkyl, aryl, heteroaryl, cycloalkyl, or heterocycloalkyl, wherein alkyl, aryl, heteroaryl, cycloalkyl, and heterocycloalkyl groups are optionally substituted by one or more substituents Y;

R4 is arylalkyl, aryloxyalkyl, arylalkoxyalkyl, heteroarylalkyl, heteroaryloxyalkyl, heteroarylalkoxyalkyl, cycloalkyl, cycloalkylalkyl, cycloalkyloxyalkyl, cycloalkylalkoxyalkyl, heterocycloalkyl, heterocycloalkyloxyalkyl, or heterocycloalkylalkoxyalkyl, which is optionally substituted by one or more substituents Y, wherein heteroaryl and heterocycloalkyl groups include one or more heteroatoms each selected from the group consisting of N, O and S, or is

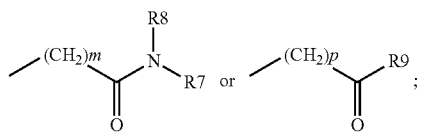

m=1-6;

R7 and R8 are independently hydrogen, aryl, heteroaryl, or Z, wherein aryl and heteroaryl groups are optionally substituted by one or more substituents Y;

or

R7 and R8 together constitute a heterocycle; which includes one or more heteroatoms each selected from the group consisting of N, O and S;

p=1-6;

R9 is aryl, heteroaryl, O—R10, or Z, wherein aryl and heteroaryl groups are optionally substituted by one or more substituents Y;

R10 is hydrogen, alkyl, aryl, or arylalkyl, wherein alkyl, aryl, and arylalkyl groups are optionally substituted by one or more substituents Y;

Z is alkyl, alkenyl, alkynyl, aryl, arylalkyl, aryloxyalkyl, arylalkoxyalkyl, arylthioalkyl, arylalkylthioalkyl, heteroaryl, heteroarylalkyl, heteroaryloxyalkyl, heteroarylalkoxyalkyl, heteroarylthioalkyl, heteroarylalkylthioalkyl, heterocycloalkyl, heterocycloalkylalkyl, heterocycloalkyloxyalkyl, heterocycloalkylalkoxyalkyl, heterocycloalkylthioalkyl, heterocycloalkylalkylthioalkyl, arylalkenyl, arylalkynyl, cycloalkyl, cycloalkylalkyl, cycloalkyloxyalkyl, cycloalkylalkoxyalkyl, cycloalkylthioalkyl, or cycloalkylalkylthioalkyl, which is optionally substituted by one or more substituents Y, wherein heteroaryl and heterocycloalkyl groups include one or more heteroatoms each selected from the group consisting of N, O and S;

Y is hydroxy, halogen, cyano, trifluoromethoxy, trifluoromethyl, carboxy, carboxy methyl, carboxyethyl, alkyl, alkoxy, alkylamino, aryl, aryl sulfonylalkyl, aryloxy, arylalkoxy, amino, NR5R6, azido, nitro, guanidino, amidino, phosphono, oxo, carbamoyl, alkylsulfonyl, alkylsulfinyl, or alkylthio, or two Y groups form a methylenedioxy; and R5 and R6 are independently hydrogen, alkyl, aryl, arylalkyl, heteroaryl, or heteroarylalkyl;

or

R5 and R6 together constitute a heterocycle, which includes one or more heteroatoms each selected from the group consisting of N, O and S.

3. A method according to claim 1, wherein in the compound of formula (I)
R1 is methyl, ethyl, propyl, or butyl, which is optionally substituted by one or more groups Y.

4. A method according to claim 1, wherein in the compound of formula (I)
R1 is not methyl or ethyl.

5. A method according to claim 1, wherein a compound of formula (I) or a pharmaceutically acceptable salt thereof is administered.

6. A method according to claim 1, wherein in the compound of formula (I)
R5 and R6 are independently hydrogen, alkyl, aryl, arylalkyl, heteroaryl, or heteroarylalkyl;

or

R5 and R6 together constitute a heterocycle; which includes one or more heteroatoms each selected from the group consisting of N, O and S.

7. A method according to claim 6, wherein in the compound of formula (I)
R4 is aryloxyalkyl, arylalkoxyalkyl, arylthioalkyl, arylalkylthioalkyl, heteroaryl, heteroarylalkyl, heteroaryloxyalkyl, heteroarylalkoxyalkyl, heteroarylthioalkyl, heteroarylalkylthioalkyl, heterocycloalkyl, heterocycloalkyloxyalkyl, heterocycloalkylalkoxyalkyl, heterocycloalkylthioalkyl, heterocycloalkylalkylthioalkyl, arylalkenyl, arylalkynyl, cycloalkyl, cycloalkylalkyl, cycloalkyloxyalkyl, cycloalkylalkoxyalkyl, cycloalkylthioalkyl, or cycloalkylalkylthioalkyl, which is optionally substituted by one or more substituents Y, wherein heteroaryl and heterocycloalkyl groups include one or more heteroatoms each selected from the group consisting of N, O and S, or is

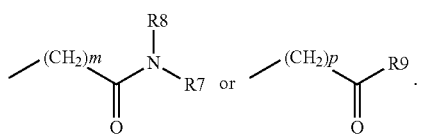

8. A method according to claim 6, wherein in the compound of formula (I)
R1 is methyl, ethyl, propyl, or butyl, which is optionally substituted by one or more groups Y.

9. A method according to claim 2, wherein in the compound of formula (I)
R5 and R6 are independently hydrogen, alkyl, aryl, arylalkyl, heteroaryl, or heteroarylalkyl.

10. A method for treating diabetes associated with lack of insulin production or for treating type II diabetes,
comprising administering to a subject in need thereof an effective amount of a compound of formula (I), or a racemic form, tautomer, enantiomer, diastereomer, epimer or polymorph thereof, or a mixture thereof, or a pharmaceutically acceptable salt thereof

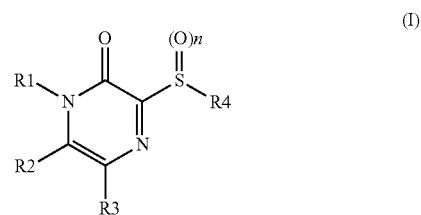

wherein
n=0, 1, or 2;
R1 is alkyl;
R2 is hydrogen;
R3 is hydrogen, halogen, alkyl, aryl, or heteroaryl,
wherein alkyl, aryl, and heteroaryl groups are optionally substituted by one or more substituents Y;
R4 is arylalkyl, aryloxyalkyl, arylalkoxyalkyl, heteroarylalkyl, heteroaryloxyalkyl, heteroarylalkoxyalkyl, heterocycloalkyl, heterocycloalkyloxyalkyl, heterocycloalkylalkoxyalkyl, cycloalkyl, cycloalkylalkyl, cycloalkyloxyalkyl, or cycloalkylalkoxyalkyl,
wherein the alkyl, aryl, heteroaryl, cycloalkyl and heterocycloalkyl groups are optionally substituted by one or more substituents Y;
wherein heteroaryl and heterocycloalkyl groups include one or more heteroatoms each selected from the group consisting of N, O and S, or is

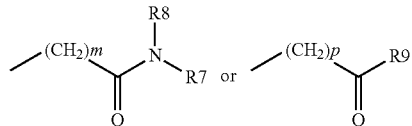

m=1-6;
R7 and R8 are independently hydrogen, aryl, heteroaryl, or Z, wherein aryl and heteroaryl groups are optionally substituted by one or more substituents Y;
or
R7 and R8 together constitute a heterocycle, which includes one or more heteroatoms each selected from the group consisting of N, O and S;
p=1-6;
R9 is aryl, heteroaryl, O—R10, or Z,
wherein aryl and heteroaryl groups are optionally substituted by one or more substituents Y;
R10 is hydrogen, alkyl, aryl, or arylalkyl,
wherein alkyl, aryl, arylalkyl groups are optionally substituted by one or more substituents Y;
Z is alkyl, alkenyl, alkynyl, aryl, arylalkyl, aryloxyalkyl, arylalkoxyalkyl, arylthioalkyl, arylalkylthioalkyl, heteroaryl, heteroarylalkyl, heteroaryloxyalkyl, heteroarylalkoxyalkyl, heteroarylthioalkyl, heteroarylalkylthio-alkyl, heterocycloalkyl, heterocycloalkylalkyl, heterocycloalkyloxyalkyl, heterocycloalkylalkoxy-alkyl, heterocycloalkylthioalkyl, heterocycloalkylalky-lthioalkyl, arylalkenyl, arylalkynyl, cycloalkyl, cycloalkylalkyl, cycloalkyloxyalkyl, cycloalkylalkoxy-alkyl, cycloalkylthioalkyl, or cycloalkylalkylthioalkyl, which is optionally substituted by one or more substituents Y, wherein heteroaryl and heterocycloalkyl groups include one or more heteroatoms each selected from the group consisting of N, O and S;

Y is hydroxy, halogen, cyano, trifluoromethoxy, trifluoromethyl, carboxy, carboxy methyl, carboxyethyl, alkyl, alkoxy, alkylamino, aryl, aryl sulfonylalkyl, aryloxy, arylalkoxy, amino, NR5R6, azido, nitro, guanidino, amidino, phosphono, oxo, carbamoyl, alkylsulfonyl, alkylsulfinyl, alkylthio, two Y groups can form a methylenedioxy; and R5 and R6 are independently hydrogen, alkyl, aryl, arylalkyl, heteroaryl, or heteroarylalkyl, wherein alkyl, aryl and heteroaryl groups are optionally substituted by one or more substituents Y;

or

R5 and R6 together constitute a heterocycle, which includes one or more heteroatoms each selected from the group consisting of N, O and S.

11. A method according to claim 10, wherein in the compound of formula (I)

R3 is Cl, Br, or phenyl, which is optionally substituted by one or more groups Y.

12. A method according to claim 10, wherein in the compound of formula (I)

R4 is benzyl, phenylethyl, phenoxyethyl, phenyl-2-oxoethyl, 2-oxo-2-piperidin-1-ylethyl, N-phenylacetamide, N-methyl-N-phenylacetamide, or N-cyclohexyl-N-methylacetamide, which is optionally substituted by one or more groups Y.

13. A method according to claim 10, wherein in the compound of formula (I)

Y is halogen, trifluoromethyl, alkyl, or alkoxy.

14. A method according to claim 10, wherein in the compound of formula (I)

R5 and R6 are independently hydrogen, alkyl, aryl, arylalkyl, heteroaryl, or heteroarylalkyl;

or

R5 and R6 together constitute a heterocycle, which includes one or more heteroatom selected from the group consisting of N, O and S.

15. A method according to claim 10, wherein a compound of formula (I) or a pharmaceutically acceptable salt thereof is administered.

16. A method for treating diabetes associated with lack of insulin production or for treating type II diabetes, comprising administering to a subject in need thereof an effective amount of a compound of formula (I), or a racemic form, tautomer, enantiomer, diastereomer, epimer or polymorph thereof, or a mixture thereof, or a pharmaceutically acceptable salt thereof

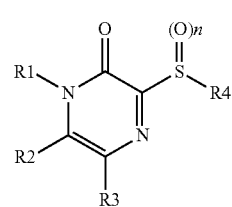

wherein n=0, 1, or 2;

R1 is alkyl, alkenyl, or alkynyl, which is optionally substituted by one or more substituents Y;

R2 is hydrogen, halogen, heteroaryl, or Z;

R3 is hydrogen, halogen, aryl, heteroaryl, or Z, wherein aryl and heteroaryl groups are optionally substituted by one or more substituents Y;

R4 is benzyl, phenylethyl, phenoxyethyl, phenyl-2-oxoethyl, 2-oxo-2-piperidin-1-ylethyl, N-phenylacetamide, N-methyl-N-phenylacetamide, or N-cyclohexyl-N-methylacetamide, which is optionally substituted by one or more groups Y;

Z is alkyl, alkenyl, alkynyl, aryl, arylalkyl, aryloxyalkyl, arylalkoxyalkyl, arylthioalkyl, arylalkylthioalkyl, heteroaryl, heteroarylalkyl, heteroaryloxyalkyl, heteroarylalkoxyalkyl, heteroarylthioalkyl, heteroarylalkylthioalkyl, heterocycloalkyl, heterocycloalkylalkyl, heterocycloalkyloxyalkyl, heterocycloalkylalkoxy-alkyl, heterocycloalkylthioalkyl, heterocycloalkylalkylthioalkyl, arylalkenyl, arylalkynyl, cycloalkyl, cycloalkylalkyl, cycloalkyloxyalkyl, cycloalkylalkoxy-alkyl, cycloalkylthioalkyl, or cycloalkylalkylthioalkyl, which is optionally substituted by one or more substituents Y, wherein heteroaryl and heterocycloalkyl groups include one or more heteroatoms each selected from the group consisting of N, O and S;

Y is hydroxy, halogen, cyano, trifluoromethoxy, trifluoromethyl, carboxy, carboxy methyl, carboxyethyl, alkyl, alkoxy, alkylamino, aryl, aryl sulfonylalkyl, aryloxy, arylalkoxy, amino, NR5R6, azido, nitro, guanidino, amidino, phosphono, oxo, carbamoyl, alkylsulfonyl, alkylsulfinyl, or alkylthio, or two Y groups form a methylenedioxy;

R5 and R6 are independently hydrogen, alkyl, aryl, arylalkyl, heteroaryl, or heteroarylalkyl;

or

R5 and R6 together constitute a heterocycle; which includes one or more heteroatoms each selected from the group consisting of N, O and S.

17. A method according to claim 16, wherein a compound of formula (I) or a pharmaceutically acceptable salt thereof is administered.

18. A method for treating diabetes associated with lack of insulin production or for treating type II diabetes, comprising administering to a subject in need thereof an effective amount of one of the following compounds 3-(benzylthio)-1-ethylpyrazin-2(1H)-one 3-benzylsulfonyl-1-ethylpyrazin-2(1H)-one 3-[(4-chlorobenzyl)sulfonyl]-1-ethylpyrazin-2(1H)-one 3-[(4-methylbenzyl)sulfonyl]-1-propylpyrazin-2(1H)-one 3-[(4-fluorobenzyl)sulfonyl]-1-propylpyrazin-2(1H)-one 3-(benzylsulfonyl)-1-propylpyrazin-2(1H)-one 1-ethyl-3-[(4-bromobenzyl)sulfonyl]pyrazin-2(1H)-one 3-[(4-chlorobenzyl)thio]-1-propylpyrazin-2(1H)-one 3-[(4-chlorobenzyl)sulfonyl]-1-propylpyrazin-2(1H)-one
3-[(3-Chlorobenzyl)sulfonyl]-1-propylpyrazin-2(1H)-one
1-methyl-3-[(4-chlorobenzyl)sulfonyl]pyrazin-2(1H)-one
1-butyl-3-[(2-fluorobenzyl)sulfonyl]pyrazin-2(1H)-one
1-butyl-3-[(3-trifluoromethylbenzyl)sulfonyl]pyrazin-2(1H)-one
1-butyl-3-[(4-chlorobenzyl)sulfonyl]pyrazin-2(1H)-one
3-{[2-(4-chlorophenyl)ethyl]sulfonyl}-1-propylpyrazin-2(1H)-one
1-ethyl-3-{[2-(4-methoxyphenoxyl)ethyl]sulfonyl}pyrazin-2(1H)-one
3-{[2-(4-chlorophenyl)-2-oxoethyl]sulfonyl}-1-ethylpyrazin-2(1H)-one
3-[(1,1'-biphenyl-4-ylmethyl)sulfonyl]-1-ethylpyrazin-2(1H)-one
3-{[2-(4-chlorophenoxyl)ethyl]sulfonyl}-1-ethylpyrazin-2(1H)-one
3-{[2-(4-methylphenyl)ethyl]sulfonyl}-1-propylpyrazin-2(1H)-one
3-{[2-(4-chlorophenyl)ethyl]sulfonyl}-1-ethylpyrazin-2(1H)-one
3-[(1,1'-biphenyl-4-ylmethyl)sulfonyl]-1-butylpyrazin-2(1H)-one
3-[(4-methoxybenzyl)sulfonyl]-1-propylpyrazin-2(1H)-one
3-[(3-Fluorobenzyl)sulfonyl]-1-methylpyrazin-2(1H)-one
3-[(2-Fluorobenzyl)sulfonyl]-1-methylpyrazin-2(1H)-one
1-Butyl-3-[(4-methoxybenzyl)sulfonyl]pyrazin-2(1H)-one
1-Ethyl-3-[(4-fluorobenzyl)sulfonyl]pyrazin-2(1H)-one
1-Ethyl-3-[(3-trifluoromethybenzyl)sulfonyl]pyrazin-2(1H)-one
1-Ethyl-3-[(3-fluorobenzyl)sulfonyl]pyrazin-2(1H)-one
1-Ethyl-3-[(2-fluorobenzyl)sulfonyl]pyrazin-2(1H)-one
1-Butyl-3-[(3-fluorobenzyl)sulfonyl]pyrazin-2(1H)-one
1-Butyl-3-[(2-methylbenzyl)sulfonyl]pyrazin-2(1H)-one
1-ethyl-3-[(2-methylbenzyl)sulfonyl]pyrazin-2(1H)-one
3-[(4-chlorobenzyl)sulfinyl]-1-ethylpyrazin-2(1H)-one
5-bromo-3-[(4-chlorobenzyl)thio]-1-ethylpyrazin-2(1H)-one
5-bromo-3-[(4-chlorobenzyl)sulfonyl]-1-ethylpyrazin-2(1H)-one
3-[(4-chlorobenzyl)sulfonyl]-1-ethyl-5-phenylpyrazin-2(1H)-one
3-[(4-chlorobenzyl)sulfonyl]-5-(4-chlorophenyl)-1-ethylpyrazin-2(1H)-one
3-[(4-chlorobenzyl)sulfonyl]-1-ethyl-5-(4-fluorophenyl)pyrazin-2(1H)-one
2-[(6-chloro-4-ethyl-3-oxo-3,4-dihydropyrazin-2-yl)thio]-N-phenyl acetamide
2-[(6-chloro-4-ethyl-3-oxo-3,4-dihydropyrazin-2-yl)sulfonyl]-N-phenylacetamide
5-chloro-1-ethyl-3-[(2-oxo-2-piperidin-1-ylethyl)sulfonyl]pyrazin-2(1H)-one
2-[(6-chloro-4-ethyl-3-oxo-3,4-dihydropyrazin-2-yl)sulfonyl]-N-methyl-N-phenylacetamide or
2-[(6-chloro-4-ethyl-3-oxo-3,4-dihydropyrazin-2-yl)sulfonyl]-N-cyclohexyl-N-methylacetamide
or a racemic form, tautomer, enantiomer, diastereomer, epimer or polymorph thereof,
or a pharmaceutically acceptable salt thereof.

19. A method according to claim 18, wherein one of the following compounds is administered
1-Ethyl-3-[(4-bromobenzyl)sulfonyl]pyrazin-2(1H)-one
1-Ethyl-3-benzylsulfonylpyrazin-2(1H)-one
1-Butyl-3-[(2-fluorobenzyl)sulfonyl]pyrazin-2(1H)-one
1-Butyl-3-[(3-trifluoromethylbenzyl)sulfonyl]pyrazin-2(1H)-one
1-Butyl-3-[(4-chlorobenzyl)sulfonyl]pyrazin-2(1H)-one
3-[(4-Chlorobenzyl)sulfonyl]-1-ethylpyrazin-2(1H)-one
3-[(4-Chlorobenzyl)sulfonyl]-1-propylpyrazin-2(1H)-one
3-[(4-Chlorobenzyl)sulfonyl]-5-(4-chlorophenyl)-1-ethylpyrazin-2(1H)-one
3-[(4-Fluorobenzyl)sulfonyl]-1-propylpyrazin-2(1H)-one
3-[(4-Methylbenzyl)sulfonyl]-1-propylpyrazin-2(1H)-one
3-{[2-(4-Chlorophenyl)ethyl]sulfonyl}-1-propylpyrazin-2(1H)-one or
5-Chloro-1-ethyl-3-[(2-oxo-2-piperidin-1-ylethyl)sulfonyl]pyrazin-2(1H)-one
or a racemic form, tautomer, enantiomer, diastereomer, epimer or polymorph thereof,
or a pharmaceutically acceptable salt thereof.

20. A method according to claim 18, wherein one of the following compounds is administered
3-(benzylthio)-1-ethylpyrazin-2(1H)-one
3-benzylsulfonyl-1-ethylpyrazin-2(1H)-one
3-[(4-chlorobenzyl)sulfonyl]-1-ethylpyrazin-2(1H)-one
3-[(4-methylbenzyl)sulfonyl]-1-propylpyrazin-2(1H)-one
3-[(4-fluorobenzyl)sulfonyl]-1-propylpyrazin-2(1H)-one
3-(benzylsulfonyl)-1-propylpyrazin-2(1H)-one
1-ethyl-3-[(4-bromobenzyl)sulfonyl]pyrazin-2(1H)-one
3-[(4-chlorobenzyl)thio]-1-propylpyrazin-2(1H)-one
3-[(4-chlorobenzyl)sulfonyl]-1-propylpyrazin-2(1H)-one
3-[(3-Chlorobenzyl)sulfonyl]-1-propylpyrazin-2(1H)-one
1-methyl-3-[(4-chlorobenzyl)sulfonyl]pyrazin-2(1H)-one
1-butyl-3-[(2-fluorobenzyl)sulfonyl]pyrazin-2(1H)-one
1-butyl-3-[(3-trifluoromethylbenzyl)sulfonyl]pyrazin-2(1H)-one
1-butyl-3-[(4-chlorobenzyl)sulfonyl]pyrazin-2(1H)-one
3-{[2-(4-chlorophenyl)ethyl]sulfonyl}-1-propylpyrazin-2(1H)-one
1-ethyl-3-{[2-(4-methoxyphenoxyl)ethyl]sulfonyl}pyrazin-2(1H)-one
3-{[2-(4-chlorophenyl)-2-oxoethyl]sulfonyl}-1-ethylpyrazin-2(1H)-one
3-[(1,1'-biphenyl-4-ylmethyl)sulfonyl]-1-ethylpyrazin-2(1H)-one
3-{[2-(4-chlorophenoxyl)ethyl]sulfonyl}-1-ethylpyrazin-2(1H)-one
3-{[2-(4-methylphenyl)ethyl]sulfonyl}-1-propylpyrazin-2(1H)-one
3-{[2-(4-chlorophenyl)ethyl]sulfonyl}-1-ethylpyrazin-2(1H)-one
3-[(1,1'-biphenyl-4-ylmethyl)sulfonyl]-1-butylpyrazin-2(1H)-one
3-[(4-methoxybenzyl)sulfonyl]-1-propylpyrazin-2(1H)-one
3-[(3-Fluorobenzyl)sulfonyl]-1-methylpyrazin-2(1H)-one
3-[(2-Fluorobenzyl)sulfonyl]-1-methylpyrazin-2(1H)-one
1-Butyl-3-[(4-methoxybenzyl)sulfonyl]pyrazin-2(1H)-one
1-Ethyl-3-[(4-fluorobenzyl)sulfonyl]pyrazin-2(1H)-one
1-Ethyl-3-[(3-trifluoromethybenzyl)sulfonyl]pyrazin-2(1H)-one
1-Ethyl-3-[(3-fluorobenzyl)sulfonyl]pyrazin-2(1H)-one
1-Ethyl-3-[(2-fluorobenzyl)sulfonyl]pyrazin-2(1H)-one
1-Butyl-3-[(3-fluorobenzyl)sulfonyl]pyrazin-2(1H)-one
1-Butyl-3-[(2-methylbenzyl)sulfonyl]pyrazin-2(1H)-one
1-ethyl-3-[(2-methylbenzyl)sulfonyl]pyrazin-2(1H)-one 3-[(4-chlorobenzyl)sulfinyl]-1-ethylpyrazin-2(1H)-one
5-bromo-3-[(4-chlorobenzyl)thio]-1-ethylpyrazin-2(1H)-one
5-bromo-3-[(4-chlorobenzyl)sulfonyl]-1-ethylpyrazin-2(1H)-one
3-[(4-chlorobenzyl)sulfonyl]-1-ethyl-5-phenylpyrazin-2(1H)-one
3-[(4-chlorobenzyl)sulfonyl]-5-(4-chlorophenyl)-1-ethylpyrazin-2(1H)-one
3-[(4-chlorobenzyl)sulfonyl]-1-ethyl-5-(4-fluorophenyl)pyrazin-2(1H)-one
2-[(6-chloro-4-ethyl-3-oxo-3,4-dihydropyrazin-2-yl)thio]-N-phenyl acetamide
2-[(6-chloro-4-ethyl-3-oxo-3,4-dihydropyrazin-2-yl)sulfonyl]-N-phenylacetamide
5-chloro-1-ethyl-3-[(2-oxo-2-piperidin-1-ylethyl)sulfonyl]pyrazin-2(1H)-one
2-[(6-chloro-4-ethyl-3-oxo-3,4-dihydropyrazin-2-yl)sulfonyl]-N-methyl-N-phenylacetamide or
2-[(6-chloro-4-ethyl-3-oxo-3,4-dihydropyrazin-2-yl)sulfonyl]-N-cyclohexyl-N-methylacetamide
or a pharmaceutically acceptable salt thereof.

21. A method according to claim 1, wherein type II diabetes is treated.

22. A method according to claim 10, wherein type II diabetes is treated.

23. A method according to claim 16, wherein type II diabetes is treated.

24. A method according to claim 18, wherein type II diabetes is treated.

* * * * *